(12) United States Patent
Asano et al.

(10) Patent No.: US 8,580,480 B2
(45) Date of Patent: Nov. 12, 2013

(54) RADIATION-SENSITIVE RESIN COMPOSITION, METHOD FOR FORMING RESIST PATTERN, POLYMER AND COMPOUND

(75) Inventors: Yusuke Asano, Tokyo (JP); Mitsuo Sato, Tokyo (JP)

(73) Assignee: JSR Corporation, Tokyo (JP)

( * ) Notice: Subject to any disclaimer, the term of this patent is extended or adjusted under 35 U.S.C. 154(b) by 1 day.

(21) Appl. No.: 13/191,416

(22) Filed: Jul. 26, 2011

(65) Prior Publication Data

US 2012/0028189 A1 Feb. 2, 2012

(30) Foreign Application Priority Data

Jul. 27, 2010 (JP) ................... 2010-168055

(51) Int. Cl.
*G03F 7/00* (2006.01)
*C08F 20/10* (2006.01)
*C07C 69/017* (2006.01)

(52) U.S. Cl.
USPC ........................... 430/270.1; 526/326; 560/64

(58) Field of Classification Search
USPC .................................. 526/242, 245
See application file for complete search history.

(56) References Cited

U.S. PATENT DOCUMENTS

2009/0186300 A1* 7/2009 Furuya et al. .............. 430/285.1

FOREIGN PATENT DOCUMENTS

| JP | 06-012452 B2 | 5/1984 |
|---|---|---|
| JP | 05-188598 | 7/1993 |
| JP | 11-176727 | 7/1999 |
| JP | 2005-352384 | 12/2005 |
| JP | 2007-204385 | 8/2007 |
| JP | 2007-304537 | 11/2007 |
| JP | 2008-088343 | 4/2008 |
| JP | 2008-111103 | 5/2008 |
| JP | 2009-019199 | 1/2009 |
| JP | 2009-074085 | 4/2009 |
| JP | 2009-134088 | 6/2009 |
| JP | 2009-139909 | 6/2009 |
| JP | 2010-032994 | 2/2010 |
| WO | WO 2007/116664 | 10/2007 |
| WO | WO 2009/051088 | 4/2009 |

OTHER PUBLICATIONS

Nishikubo et al., "Convenient Syntheses of Cyclic Carbonates by new Reaction of Oxiranes with β-Butyrolactone", Tetrahedron Letters, 1986, pp. 3741-3744, vol. 27, No. 32.

Vincenzo Calò et al., "Cyclic Carbonate Formation from Carbon Dioxide and Oxiranes in Tetrabutylammonium Halides as Solvents and Catalysts", Organic Letters, 2002, pp. 2561-2563, vol. 4, No. 15.

* cited by examiner

*Primary Examiner* — Cynthia H Kelly
*Assistant Examiner* — Alyssa L Cepluch
(74) *Attorney, Agent, or Firm* — Ditthavong Mori & Steiner, P.C.

(57) ABSTRACT

A radiation-sensitive resin composition includes (A) a fluorine-containing compound that includes a group shown by the following formula (1), and (B) a photoacid generator.

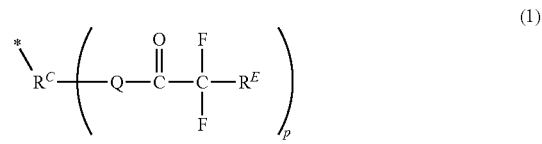

(1)

wherein $R^C$ represents a (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms, p is an integer from 1 to 5, provided that a plurality of Q and a plurality of $R^E$ may respectively be either the same or different when p is an integer from 2 to 5, and "*" indicates a bonding hand.

11 Claims, No Drawings

RADIATION-SENSITIVE RESIN COMPOSITION, METHOD FOR FORMING RESIST PATTERN, POLYMER AND COMPOUND

CROSS-REFERENCE TO RELATED APPLICATIONS

The present application claims priority under 35 U.S.C. §119 to Japanese Patent Application No. 2010-168055, filed Jul. 27, 2010. The contents of this application are incorporated herein by reference in their entirety.

BACKGROUND OF THE INVENTION

1. Field of the Invention

The invention relates to a radiation-sensitive resin composition, a method for forming a resist pattern, a polymer, and a compound.

2. Discussion of the Background

When producing a semiconductor device or the like, a resist film formed on a substrate is exposed via a mask pattern, and subjected to alkali development to form a fine resist pattern. Technology that utilizes a chemically-amplified resist that contains a photoacid generator that generates an acid upon irradiation as a resist film-forming resin composition has been known.

A further reduction in line width has been desired in the field of microfabrication, and liquid immersion lithography has been proposed to deal with such a demand. Liquid immersion lithography exposes a resist film via an immersion medium that has a refractive index higher than that of air and is provided between the lens of the exposure system and the resist film. Liquid immersion lithography makes it possible to achieve higher resolution even if a light source having the same wavelength is used (see Japanese Patent Application Publication (KOKAI) No. 11-176727, for example).

When using liquid immersion lithography, however, the composition that forms the resist film may be eluted into the immersion medium when the resist film has come in contact with the immersion medium. In this case, a deterioration in performance of the resist film, contamination of the exposure system (e.g., lens), or a decrease in resolution of the resist may occur. Moreover, since scan exposure is continuously performed at a high speed, droplets of the immersion medium tend to remain on the surface of the resist film, so that watermark defects may occur. Therefore, it is desirable that the surface of the resist film have high hydrophobicity.

Technology that incorporates a compound including a functional group that is hydrophobic during liquid immersion lithography, but becomes hydrophilic during alkali development, in a resist-forming resin composition has been developed (see Japanese Patent Application Publication (KOKAI) No. 2009-139909, for example). Japanese Patent Application Publication (KOKAI) No. 2009-139909 (see examples) discloses a compound that includes a benzene ring in which a fluoroacyl group is introduced into the side chain of an acrylic polymer or the like. In the compound disclosed in Japanese Patent Application Publication (KOKAI) No. 2009-139909, the fluorine atom is bonded to the carbon atom at the β position of the fluoroacyl group. The compound is unevenly distributed in the surface area of the resist film, so that the surface of the resist film exhibits hydrophobicity due to the fluorine atom during liquid immersion lithography, and exhibits hydrophilicity during alkali development due to a hydrophilic group produced via a reaction with the developer.

SUMMARY OF THE INVENTION

According to one aspect of the invention, a radiation-sensitive resin composition includes (A) a fluorine-containing compound that includes a group shown by a formula (1), and (B) a photoacid generator,

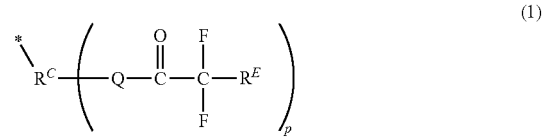

wherein $R^C$ represents a (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms, p is an integer from 1 to 5, provided that a plurality of Q and a plurality of $R^E$ may respectively be either the same or different when p is an integer from 2 to 5, and "*" indicates a bonding hand.

According to another aspect of the invention, a polymer includes a repeating unit shown by a formula (1p),

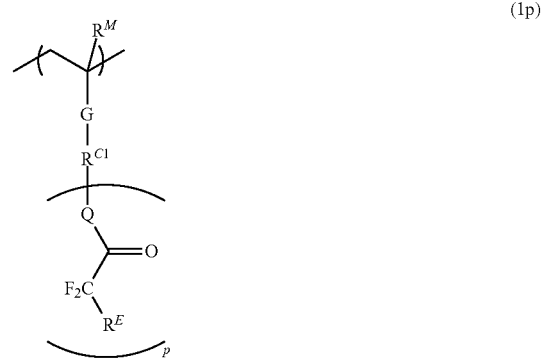

wherein $R^M$ represents a hydrogen atom, a halogen atom, an alkyl group having 1 to 5 carbon atoms, or an alkyl halide group having 1 to 5 carbon atoms, G represents a single bond, —(CH$_2$)$_b$—, —CO—O—, or —CO—NH— (wherein b is 1 or 2), $R^{C1}$ represents a (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms, and p is an integer from 1 to 5, provided that a plurality of Q and a plurality of $R^E$ may respectively be either the same or different when p is an integer from 2 to 5.

According to another aspect of the invention, a compound is shown by a formula (1m),

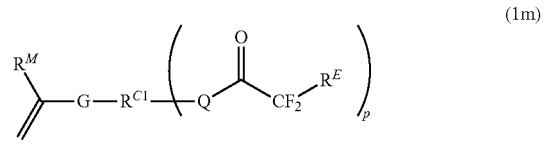

wherein $R^M$ represents a hydrogen atom, a halogen atom, an alkyl group having 1 to 5 carbon atoms, or an alkyl halide group having 1 to 5 carbon atoms, G represents a single bond, $-(CH_2)_b-$, $-CO-O-$, or $-CO-NH-$ (wherein b is 1 or 2), $R^{C1}$ represents a (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms, and p is an integer from 1 to 5, provided that a plurality of Q and a plurality of $R^E$ may respectively be either the same or different when p is an integer from 2 to 5.

DESCRIPTION OF THE EMBODIMENTS

A radiation-sensitive resin composition according to one embodiment of the invention includes (A) a fluorine-containing compound that includes a group shown by the following formula (1), and (B) a photoacid generator.

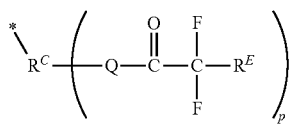

(1)

wherein $R^C$ represents a substituted or unsubstituted (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms that may include a fluorine atom, p is an integer from 1 to 5, provided that a plurality of Q and a plurality of $R^E$ may respectively be either the same or different when p is an integer from 2 to 5, and "*" indicates a bonding hand.

In the fluorine-containing compound (A), the fluorine atoms are bonded to the carbon atom present at the a position with respect to the carbonyl group in the formula (1). Therefore, the carbon atom of the carbonyl group exhibits high reactivity, so that the group $-CO-CF_2-R_E$ dissociates promptly under alkaline conditions to produce a hydrophilic group (-QH). The fluorine-containing compound (A) thus exhibits a high rate of reaction with an alkaline developer as compared with a compound in which the fluorine atoms are bonded to the carbon atom present at the β position with respect to the carbonyl group. Therefore, when forming a resist film using the composition that includes the fluorine-containing compound (A), the surface of the resist film exhibits hydrophobicity due to the fluorine atom included in the fluorine-containing compound (A), and a hydrophilic group (-QH) is promptly produced when the resist film is subjected to alkaline conditions, so that the surface of the resist film promptly changes from a hydrophobic surface to a hydrophilic surface. As a result, impurities (e.g., development residue) rarely adhere to the surface of the film during alkali development. Moreover, since the alkaline developer is promptly spread over the surface of the resist film when the alkaline developer has come in contact with the surface of the resist film, the resist film can be advantageously developed. Therefore, the composition according to one embodiment of the invention makes it possible to form a resist film that can suppress occurrence of development defects as much as possible.

It is preferable that $R^E$ in the formula (1) represent a hydrogen atom or an unsubstituted hydrocarbon group having 1 to 10 carbon atoms. According to this configuration, since $R^E$ does not include a fluorine atom, it is possible to prevent a situation in which the reactivity of the carbon atom of the carbonyl group in the formula (1) increases to a large extent.

Therefore, a situation in which the fluorine-containing compound (A) is dissolved in an immersion medium (e.g., water) during liquid immersion lithography can be prevented.

It is preferable that the fluorine-containing compound (A) be a polymer that includes a repeating unit shown by the following formula (1p).

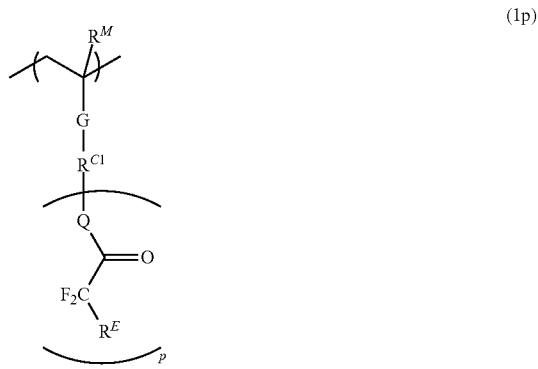

(1p)

wherein $R^M$ represents a hydrogen atom, a halogen atom, an alkyl group having 1 to 5 carbon atoms, or an alkyl halide group having 1 to 5 carbon atoms, G represents a single bond, $-(CH_2)_b-$, $-CO-O-$, or $-CO-NH-$ (wherein b is 1 or 2), $R^{C1}$ represents a substituted or unsubstituted (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms that may include a fluorine atom, and p is an integer from 1 to 5, provided that a plurality of Q and a plurality of $R^E$ may respectively be either the same or different when p is an integer from 2 to 5.

When the fluorine-containing compound (A) is a polymer, the hydrophobicity of the surface of the resist film can be easily improved. Moreover, since the aromatic ring remains in the side chain after alkali development, and remains in the alkali-insoluble area (unexposed area (positive-tone) or exposed area (negative-tone)) in a state in which the rigidity of the polymer is maintained, the resist film exhibits excellent etching resistance in the etching step after development.

It is preferable that the fluorine-containing compound (A) be a polymer that includes a repeating unit shown by a formula that is selected from the group consisting of the following formulas (1p-1) to (1p-3).

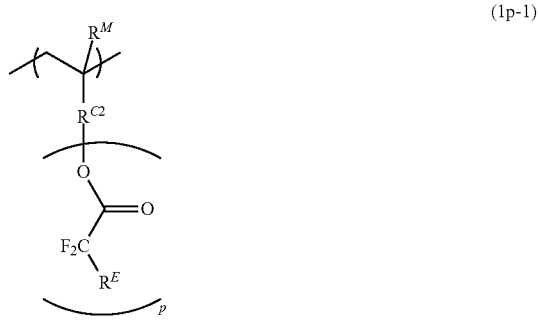

(1p-1)

-continued (1p-2)

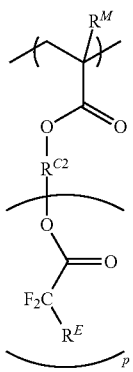

(1p-3)

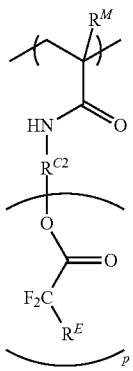

wherein $R^M$ represents a hydrogen atom, a halogen atom, an alkyl group having 1 to 5 carbon atoms, or an alkyl halide group having 1 to 5 carbon atoms, $R^{C2}$ represents a substituted or unsubstituted (p+1)-valent benzene ring, $R^E$ represents a hydrogen atom or a hydrocarbon group having 1 to 10 carbon atoms that may include a fluorine atom, and p is an integer from 1 to 5, provided that a plurality of $R^E$ may be either the same or different when p is an integer from 2 to 5.

When the ring skeleton of the aromatic ring group of the fluorine-containing compound (A) is a benzene ring, the fluorine-containing compound (A) can be easily produced.

It is preferable that the fluorine-containing compound (A) be a polymer that includes a repeating unit shown by a formula that is selected from the group consisting of the following formulas (1p-1) to (1p-3-1).

(1p-1-1)

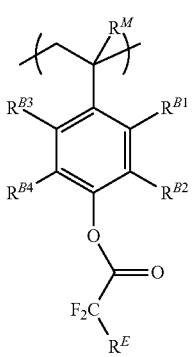

-continued (1p-2-1)

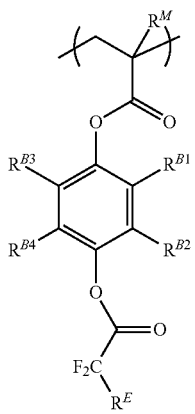

(1p-3-1)

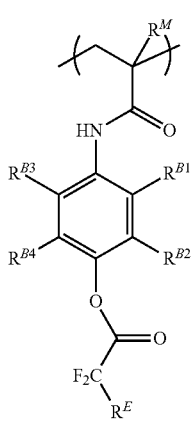

wherein $R^{B1}$ to $R^{B4}$ individually represent a hydrogen atom, a fluorine atom, —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN, or —$R^{P2}$—COOH (wherein $R^{P1}$ represents a monovalent chain-like saturated hydrocarbon group having 1 to 10 carbon atoms, a monovalent alicyclic saturated hydrocarbon group having 3 to 20 carbon atoms, or a monovalent aromatic hydrocarbon group having 6 to 30 carbon atoms, provided that some or all of the hydrogen atoms of these groups may be substituted with a fluorine atom, and $R^{P2}$ represents a single bond, a divalent chain-like saturated hydrocarbon group having 1 to 10 carbon atoms, a divalent alicyclic saturated hydrocarbon group having 3 to 20 carbon atoms, a divalent aromatic hydrocarbon group having 6 to 30 carbon atoms, or a group obtained by substituting some or all of the hydrogen atoms of these groups with a fluorine atom), and $R^E$ represents a hydrogen atom or a hydrocarbon group having 1 to 10 carbon atoms that may include a fluorine atom.

This makes it possible to facilitate production of the fluorine-containing compound (A) while achieving the above excellent effects.

It is preferable that the radiation-sensitive resin composition further include (C) a polymer that includes an acid-labile group, and the fluorine-containing polymer (A) have a fluorine atom content higher than that of the polymer (C). When the radiation-sensitive resin composition includes the polymer (C), the fluorine-containing compound (A) is more easily unevenly distributed in the surface area of the resulting resist film. Therefore, the group shown by the formula (1) is unevenly distributed in the surface area of the resist film, so that the hydrophobic surface of the resist film promptly becomes hydrophilic during alkali development.

A method for forming a resist pattern according to one embodiment of the invention includes forming a resist film on a support using the radiation-sensitive resin composition, subjecting the resist film to liquid immersion lithography, and developing the resist film subjected to liquid immersion lithography to form a resist pattern.

Since the method according to one embodiment of the invention utilizes the above radiation-sensitive resin composition, the surface of the film exhibits a high draining capability during liquid immersion lithography, and the surface wettability increases within a short time during development. Therefore, an excellent resist pattern can be efficiently formed.

A polymer according to one embodiment of the invention includes a repeating unit shown by the following formula (1p).

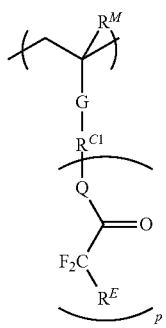

wherein $R^M$ represents a hydrogen atom, a halogen atom, an alkyl group having 1 to 5 carbon atoms, or an alkyl halide group having 1 to 5 carbon atoms, G represents a single bond, —$(CH_2)_b$—, —CO—O—, or —CO—NH— (wherein b is 1 or 2), $R^{C1}$ represents a substituted or unsubstituted (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms that may include a fluorine atom, and p is an integer from 1 to 5, provided that a plurality of Q and a plurality of $R^E$ may respectively be either the same or different when p is an integer from 2 to 5.

A compound according to one embodiment of the invention is shown by the following formula (1m).

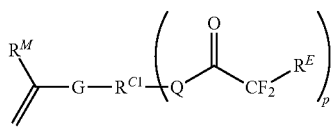

wherein $R^M$ represents a hydrogen atom, a halogen atom, an alkyl group having 1 to 5 carbon atoms, or an alkyl halide group having 1 to 5 carbon atoms, G represents a single bond, —$(CH_2)_b$—, —CO—O—, or —CO—NH— (wherein b is 1 or 2), $R^{C1}$ represents a substituted or unsubstituted (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms that may include a fluorine atom, and p is an integer from 1 to 5, provided that a plurality of Q and a plurality of $R^E$ may respectively be either the same or different when p is an integer from 2 to 5.

A radiation-sensitive resin composition that achieves above effects and advantages can be obtained by utilizing the above polymer or compound.

The term "hydrocarbon group" used herein includes a chain-like hydrocarbon group, an alicyclic hydrocarbon group, and an aromatic hydrocarbon group. The hydrocarbon group may be a saturated hydrocarbon group or an unsaturated hydrocarbon group.

The term "chain-like hydrocarbon group" used herein refers to a hydrocarbon group that does not include a cyclic structure, but includes only a chain-like structure. The term "chain-like hydrocarbon group" used herein includes a linear hydrocarbon group and a branched hydrocarbon group.

The term "aliphatic hydrocarbon group" used herein refers to a hydrocarbon group that does not include an aromatic ring structure. The term "aliphatic hydrocarbon group" used herein includes a linear hydrocarbon group, a branched hydrocarbon group, and an alicyclic hydrocarbon group.

The term "alicyclic hydrocarbon group" used herein refers to a hydrocarbon group that includes only an alicyclic hydrocarbon structure as a cyclic structure, and does not include an aromatic ring structure. Note that the alicyclic hydrocarbon group need not necessarily include only an alicyclic hydrocarbon structure, but may also include a chain-like structure.

The term "aromatic hydrocarbon group" used herein refers to a hydrocarbon group that includes an aromatic ring structure. Note that the aromatic hydrocarbon group need not necessarily include only an aromatic ring structure, but may also include a chain structure or an alicyclic hydrocarbon structure.

The term "acid-labile group" used herein refers to a group that substitutes a hydrogen atom of a polar functional group (e.g., hydroxyl group or carboxyl group), and dissociates in the presence of an acid.

The term "alkali-labile group" used herein refers to a group that substitutes a hydrogen atom of a polar functional group (e.g., hydroxyl group or carboxyl group), and dissociates in the presence of an alkali (e.g., 2.38 mass % tetramethylammonium hydroxide aqueous solution (23° C.)).

Exemplary embodiments of the invention are described below. A radiation-sensitive resin composition according to one embodiment of the invention includes (A) a fluorine-containing compound and (B) an acid generator. The composition may include (C) a polymer as a preferable optional component, and may also include (D) an acid diffusion controller, (E) a solvent, (F) an additive, or the like as an additional optional component. Each component is described below.

<Fluorine-Containing Compound (A)>

The fluorine-containing compound (A) according to one embodiment of the invention includes a group shown by the following formula (1).

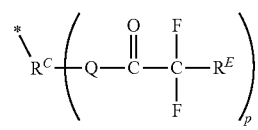

wherein $R^C$ represents a substituted or unsubstituted (p+1)-valent aromatic ring group, Q represents a linking group obtained by removing one hydrogen atom from a monovalent hydrophilic group, $R^E$ represents a hydrogen atom or a hydrocarbon group having 1 to 10 carbon atoms that may include a fluorine atom, p is an integer from 1 to 5, provided that a plurality of Q and a plurality of $R^E$ may respectively be either the same or different when p is an integer from 2 to 5, and "*" indicates a bonding hand.

$R^C$ in the formula (1) represents an aromatic ring group, and preferably an aromatic hydrocarbon group. The number of carbon atoms of the ring skeleton of the aromatic hydrocarbon group is preferably 6 to 15. Specific examples of such a ring skeleton include a benzene ring, a naphthalene ring, a phenanthrene ring, an anthracene ring, and the like. It is preferable that the aromatic ring group include a benzene ring as the ring skeleton from the viewpoint of ease of production.

The aromatic ring group represented by $R^C$ may be substituted with a substituent. Examples of the substituent include —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN, and —$R^{P2}$—COOH (wherein $R^{P1}$ represents a monovalent chain-like saturated hydrocarbon group having 1 to 10 carbon atoms, a monovalent alicyclic saturated hydrocarbon group having 3 to 20 carbon atoms, or a monovalent aromatic hydrocarbon group having 6 to 30 carbon atoms, provided that some or all of the hydrogen atoms of these groups may be substituted with a fluorine atom, and $R^{P2}$ represents a single bond, a divalent chain-like saturated hydrocarbon group having 1 to 10 carbon atoms, a divalent alicyclic saturated hydrocarbon group having 3 to 20 carbon atoms, a divalent aromatic hydrocarbon group having 6 to 30 carbon atoms, or a group obtained by substituting some or all of the hydrogen atoms of these groups with a fluorine atom). Note that some or all of the hydrogen atoms of the aromatic ring group represented by $R^C$ may be substituted with a fluorine atom. The aromatic ring group represented by $R^C$ may be substituted with one or more of one type of substituent, or may be substituted with one or more of each of a plurality of types of substituent.

The monovalent hydrophilic group that produces the linking group represented by Q includes at least one hydrogen atom. Examples of the monovalent hydrophilic group include a hydroxyl group (—OH), a carboxyl group (—C(=O)OH), an amino group (—NH$_2$), and the like. Q represents a linking group obtained by removing one hydrogen atom from a monovalent hydrophilic group. For example, Q represents —O— when the monovalent hydrophilic group is —OH. Q represents —C(=O)O— when the monovalent hydrophilic group is —C(=O)OH. Q represents —NH— when the monovalent hydrophilic group is —NH$_2$. Q preferably represents —O— or —C(=O)O—, and more preferably —O—.

One of the two bonding hands of the linking group represented by Q is bonded to the aromatic ring group ($R^C$). The other bonding hand of the linking group represented by Q is bonded to the carbonyl group shown in the formula (1).

When $R^E$ represents a hydrocarbon group that may include a fluorine atom, the hydrocarbon group may be an aliphatic hydrocarbon group or an aromatic hydrocarbon group.

When $R^E$ represents an aliphatic hydrocarbon group, the aliphatic hydrocarbon group may be a saturated hydrocarbon group or an unsaturated hydrocarbon group. $R^E$ preferably represents a saturated hydrocarbon group (i.e., an alkyl group, a cycloalkyl group, or a combination of an alkyl group and a cycloalkyl group).

The alkyl group represented by $R^E$ may be linear or branched. The number of carbon atoms of the linear alkyl group is 1 to 10, preferably 1 to 6, and more preferably 1 to 3. The number of carbon atoms of the branched alkyl group is 3 to 10. The branched alkyl group is preferably a tertiary alkyl group.

The number of carbon atoms of the cycloalkyl group represented by $R^E$ is 3 to 10. Examples of the cycloalkyl group include groups obtained by removing one hydrogen atom from a monocycloalkane or a polycycloalkane (e.g., bicycloalkane or tricycloalkane).

Examples of a combination of at least one of a linear alkyl group and a branched alkyl group and a cycloalkyl group include a group in which a cycloalkyl group is bonded to a linear or branched alkyl group as a substituent, a group in which a linear or branched alkyl group is bonded to a cycloalkyl group as a substituent, and the like.

Examples of the aromatic hydrocarbon group represented by $R^E$ include a phenyl group, a substituted phenyl group, a naphthyl group, and the like.

When $R^E$ represents a hydrocarbon group, the hydrocarbon group is preferably an aliphatic hydrocarbon group, more preferably a saturated hydrocarbon group, and still more preferably a methyl group.

When $R^E$ represents a hydrocarbon group, some or all of the hydrogen atoms of the hydrocarbon group may be substituted with a halogen atom (e.g., fluorine atom) or the like. $R^E$ preferably represents a hydrocarbon group that does not include a fluorine atom, or a hydrogen atom. This makes it possible to prevent a situation in which the reactivity of the carbon atom of the carbonyl group in the formula (1) increases to a large extent. Therefore, a situation in which the fluorine-containing compound (A) is dissolved in an immersion medium (e.g., water) during liquid immersion lithography can be prevented. Moreover, the storage stability of the fluorine-containing compound (A) can be improved.

When the aromatic ring group represented by $R^C$) is substituted with a fluorine atom, it is preferable that some or all of the hydrogen atoms of the hydrocarbon group represented by $R^E$ be substituted with a fluorine atom. This reduces the electron density of the carbon atom of the carbonyl group, so that the reactivity of the carbon atom increases when subjected to alkaline conditions.

p in the formula (1) is preferably an integer from 1 to 3, and more preferably 1, from the viewpoint of ease of production.

It suffices that the fluorine-containing compound (A) include the group shown by the formula (1). The structure of the fluorine-containing compound (A) is not particularly limited. For example, the fluorine-containing compound (A) may be a low-molecular-weight compound (non-polymer) that includes the group shown by the formula (1) (hereinafter may be referred to as "specific low-molecular-weight compound"), or may be a polymer compound (polymer) that includes the group shown by the formula (1) in the side chain.

<Low-Molecular-Weight Compound>

When the fluorine-containing compound (A) is a low-molecular-weight compound, the aromatic ring group represented by $R^C$ in the formula (1) is preferably bonded to a group that includes a polymerizable group. The term "polymerizable group" refers to a group that makes it possible to produce a polymer using a low-molecular-weight compound via radical polymerization or the like. A polymerizable group generally used for a monomer, a group that includes an ethylenically unsaturated double bond, or the like may be used.

The group that includes a polymerizable group may include only a polymerizable group, or may include a polymerizable group and a group other than the polymerizable group. Examples of a group that includes a polymerizable group and a group other than the polymerizable group include a group that includes a polymerizable group and a divalent linking group. Examples of the divalent linking group include a divalent hydrocarbon group, a divalent group that includes a heteroatom, and the like.

An alkanediyl group having 1 to 10 carbon atoms is preferable as the divalent hydrocarbon group.

The term "heteroatom" refers to an atom other than a carbon atom and a hydrogen atom. Examples of the heteroatom include an oxygen atom, a nitrogen atom, a sulfur atom, a halogen atom, and the like. Examples of the group that includes a heteroatom include —O—, —C(=O)—, —C(=O)—O—, —NH—, —NR— (wherein R represents an alkyl group), —NH—C(=O)—, =N—, a combination of any of these groups and a divalent hydrocarbon group, and the like.

Examples of a preferable low-molecular-weight compound include a compound shown by the following formula (1m).

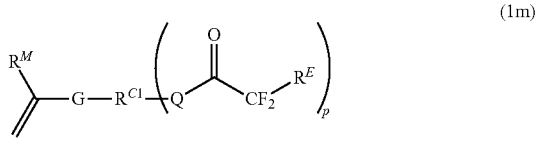

(1m)

wherein $R^M$ represents a hydrogen atom, a halogen atom, an alkyl group having 1 to 5 carbon atoms, or an alkyl halide group having 1 to 5 carbon atoms, G represents a single bond, —(CH$_2$)$_b$—, —CO—O—, or —CO—NH— (wherein b is 1 or 2), $R^{C1}$ represents a substituted or unsubstituted (p+1)-valent aromatic ring group, and $R^E$ and p are the same as defined for the formula (1).

Examples of the halogen atom represented by $R^M$ include a fluorine atom, a chlorine atom, a bromine atom, an iodine atom, and the like. Among these, a fluorine atom is preferable. Examples of the alkyl halide group represented by $R^M$ include groups obtained by substituting some or all of the hydrogen atoms of an alkyl group with a halogen atom. Examples of the halogen atom include a fluorine atom, a chlorine atom, a bromine atom, an iodine atom, and the like. Among these, a fluorine atom is preferable. $R^M$ preferably represents a hydrogen atom or an alkyl group, and more preferably a hydrogen atom or a methyl group.

b is preferably 1. G preferably represents a single bond, —CO—O—, or —CO—NH—.

Examples of the aromatic ring group represented by $R^{C1}$ include the aromatic ring groups mentioned above in connection with $R^C$ in the formula (1). Examples of a substituent that may substitute the aromatic ring group represented by $R^{C1}$ include the substituents that may substitute the aromatic ring group represented by $R^C$ in the formula (1). Note that only some of the hydrogen atoms of the aromatic ring group represented by $R^{C1}$ may be substituted with a substituent, or all of the hydrogen atoms of the aromatic ring group represented by $R^{C1}$ may be substituted with a substituent.

When the fluorine-containing compound (A) is a low-molecular-weight compound, specific examples of a preferable low-molecular-weight compound include compounds shown by the following formulas (1m-1), (1m-2), and (1m-3).

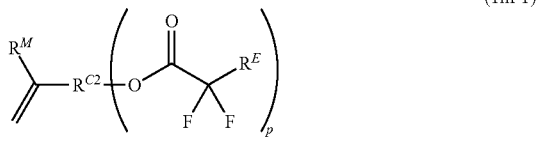

(1m-1)

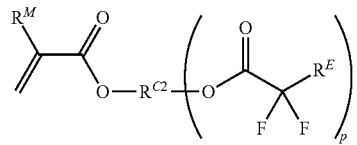

(1m-2)

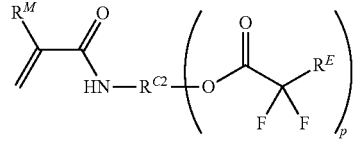

(1m-3)

wherein $R^{C2}$ represents a substituted or unsubstituted (p+1)-valent benzene ring, and $R^M$, $R^E$, and p are the same as defined for the formula (1m).

Examples of a substituent that may substitute the benzene ring represented by $R^{C2}$ include the substituents that may substitute the aromatic ring group represented by $R^C$ in the formula (1). Note that only some of the hydrogen atoms of the benzene ring represented by $R^{C2}$ may be substituted with a substituent, or all of the hydrogen atoms of the benzene ring represented by $R^{C2}$ may be substituted with a substituent.

Specific examples of the compounds shown by the formulas (1m-1) to (1m-3) include compounds shown by the following formulas (1m-1-1) to (1m-1-3), (1m-2-1) to (1m-2-3), and (1m-3-1) to (1m-3-3), respectively.

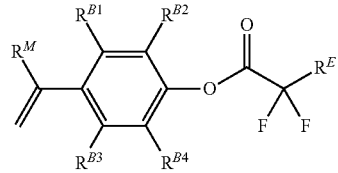

(1m-1-1)

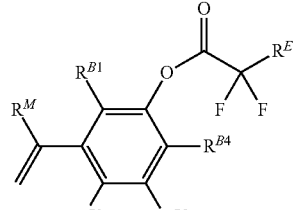

(1m-1-2)

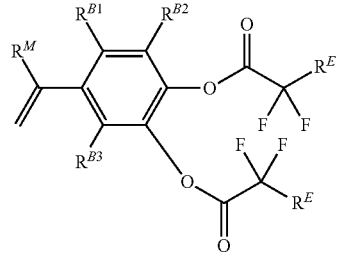

(1m-1-3)

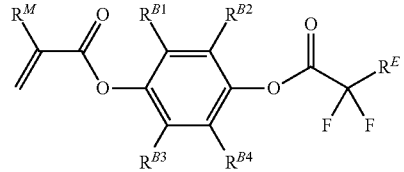

(1m-2-1)

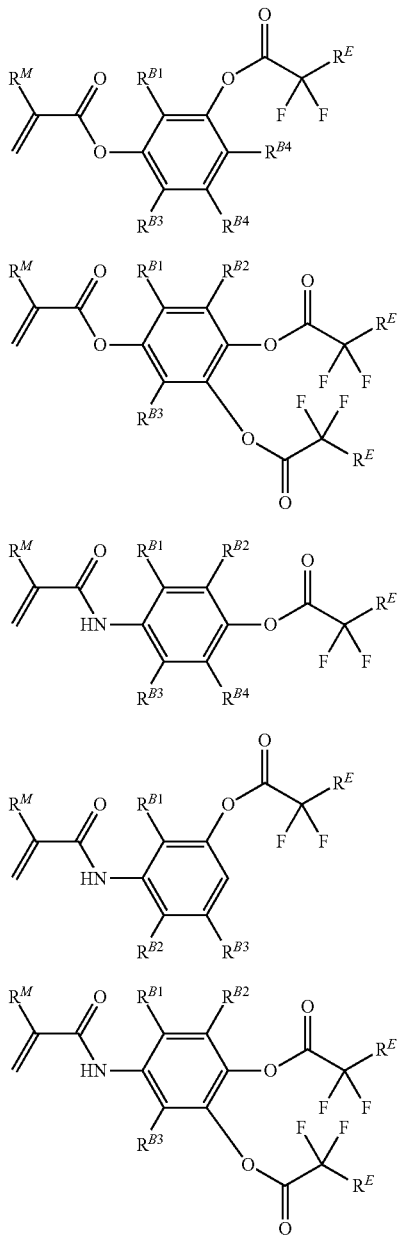

wherein $R^{B1}$ to $R^{B4}$ individually represent a hydrogen atom, a fluorine atom, or a substituent that may substitute the aromatic ring group represented by $R^C$, and $R^M$ and $R^E$ are the same as defined for the formula (1m).

Specific examples of the substituent represented by $R^{B1}$ to $R^{B4}$ include those mentioned above in connection with $R^C$.

$R^{B1}$ to $R^{B4}$ preferably represent a hydrogen atom or a fluorine atom. It is preferable that all of $R^{B1}$ to $R^{B4}$ represent a fluorine atom or all of $R^{B1}$ to $R^{B4}$ represent a hydrogen atom from the viewpoint of ease of production.

When all of $R^{B1}$ to $R^{B4}$ represent a fluorine atom, $R^E$ preferably represents a hydrocarbon group that includes a fluorine atom. When all of $R^{B1}$ to $R^{B4}$ represent a hydrogen atom, $R^E$ preferably represents a hydrogen atom or a hydrocarbon group that does not include a fluorine atom.

When the fluorine-containing compound (A) is a low-molecular-weight compound, the compounds shown by the formulas (1m-1-1), (1m-1-2), (1m-2-1), (1m-2-2), (1m-3-1), and (1m-3-2) are preferable, and the compounds shown by the formulas (1m-1-1), (1m-2-1), and (1m-3-1) are more preferable, from the viewpoint of ease of production.

Specific examples of the low-molecular-weight compounds shown by the formulas (1m-1-1), (1m-2-1), and (1m-3-1) include compounds shown by the following formulas (1m-1-1a) to (1m-1-1f), (1m-2-1a) to (1m-2-1f), and (1m-3-1a) to (1m-3-1f), respectively.

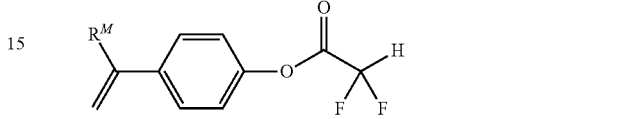

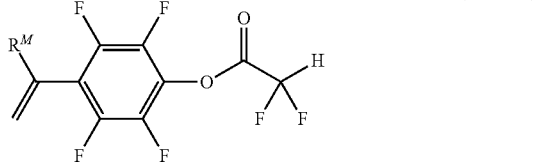

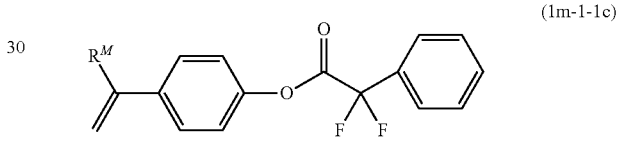

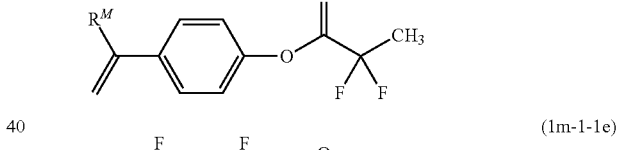

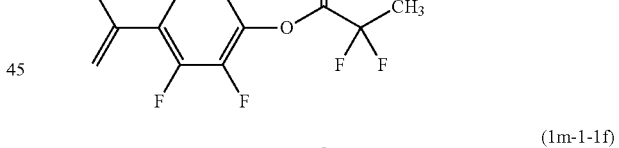

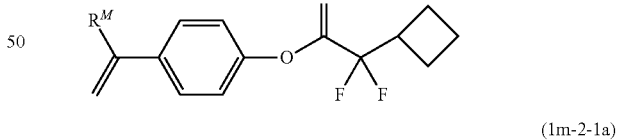

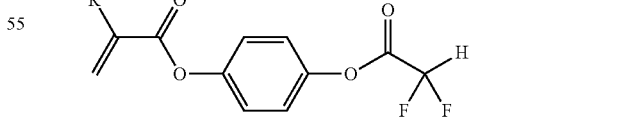

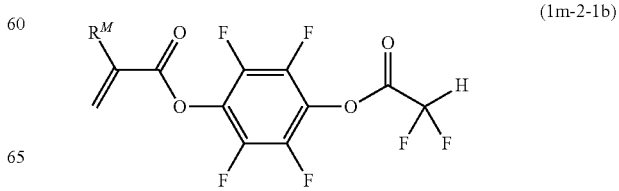

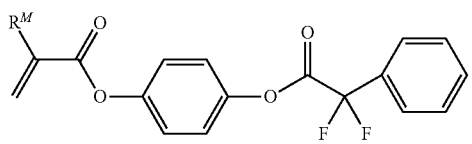 (1m-2-1c)

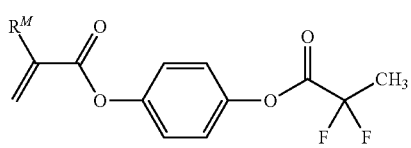 (1m-2-1d)

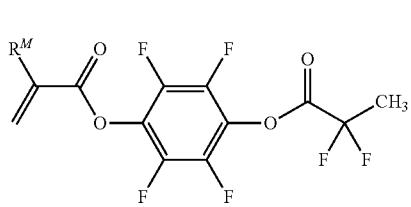 (1m-2-1e)

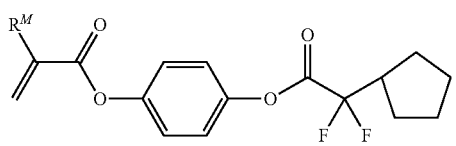 (1m-2-1f)

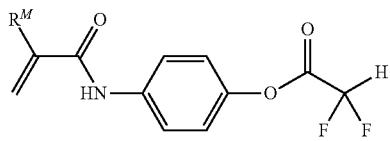 (1m-3-1a)

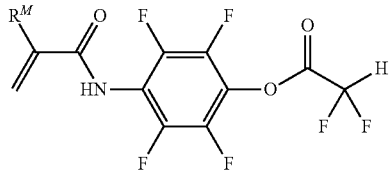 (1m-3-1b)

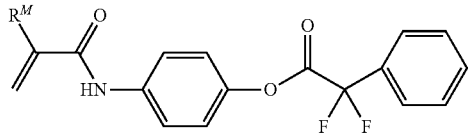 (1m-3-1c)

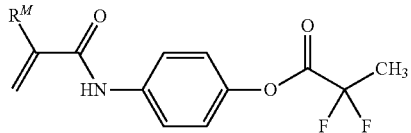 (1m-3-1d)

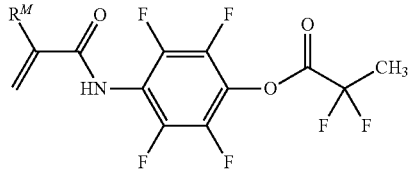 (1m-3-1e)

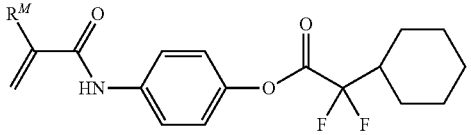 (1m-3-1f)

wherein $R^M$ is the same as defined for the formula (1m).

The specific low-molecular-weight compound may preferably be used as an additive for a radiation-sensitive resin composition that is used as a resist composition for liquid immersion lithography. When the specific low-molecular-weight compound includes a polymerizable group (see the formula (1m)), a homopolymer may be produced by polymerizing the low-molecular-weight compound. Alternatively, a copolymer may be produced by copolymerizing the specific low-molecular-weight compound with another polymerizable compound. These polymers may also suitably be used as an additive for the radiation-sensitive resin composition. A case where the fluorine-containing compound (A) is a polymer is described in detail below.

<Polymer>

When the fluorine-containing compound (A) is a polymer, the polymer preferably includes a repeating unit shown by the following formula (1p) (hereinafter may be referred to as "repeating unit (a1)").

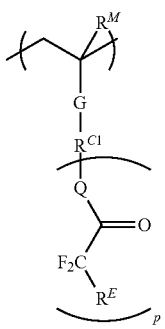 (1p)

wherein $R^M$, G, $R^{C1}$, Q, $R^E$, and p are the same as defined for the formula (1m).

<Repeating Unit (a1)>

Specific examples of a preferable repeating unit (a1) include repeating units shown by the following formulas (1p-1), (1p-2), and (1p-3).

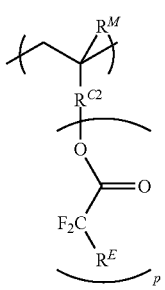 (1p-1)

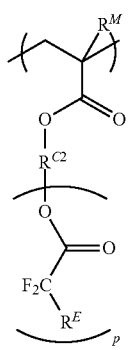 (1p-2)
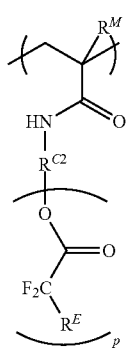 (1p-3)
wherein $R^M$, $R^{C2}$, $R^E$, and p are the same as defined for the formulas (1m-1) to (1m-3).
Specific examples of the repeating units shown by the formulas (1p-1) to (1p-3) include repeating units shown by the following formulas (1p-1) to (1p-1-3), (1p-2-1) to (1p-2-3), and (1p-3-1) to (1p-3-3), respectively.
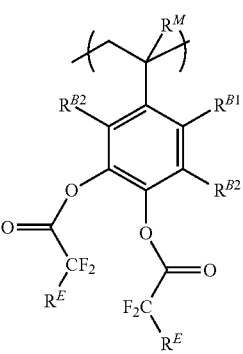 (1p-1-3)
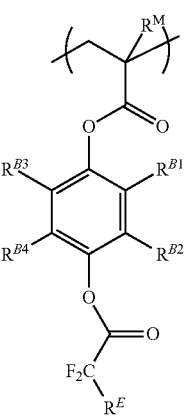 (1p-1-1)
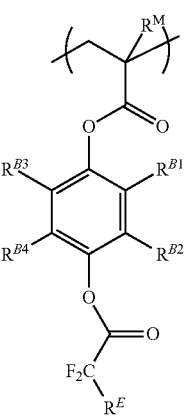 (1p-1-2)
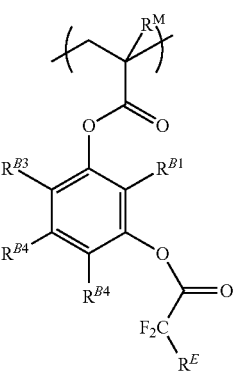 (1p-2-1)
(1p-2-2)
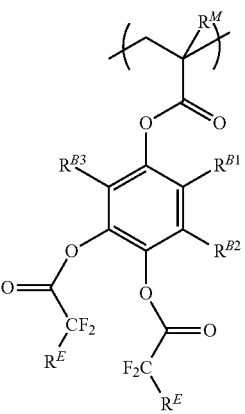 (1p-2-3)

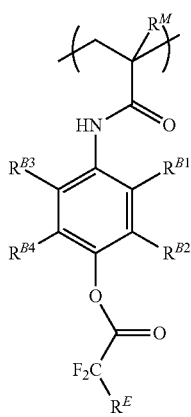
(1p-3-1)

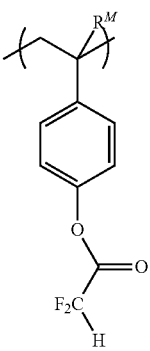
(1p-1-1a)

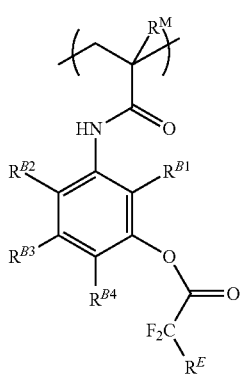
(1p-3-2)

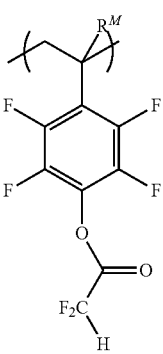
(1p-1-1b)

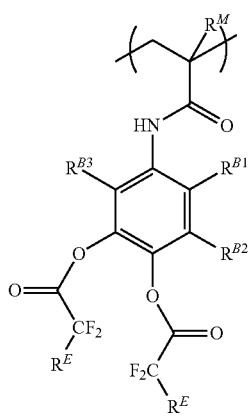
(1p-3-3)

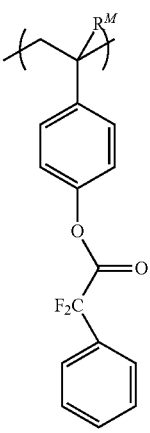
(1p-1-1c)

wherein $R^M$, $R^E$, and $R^{B1}$ to $R^{B4}$ are the same as defined for the formulas (1m-1-1) to (1m-3-3).

When the fluorine-containing compound (A) is a polymer, the repeating units shown by the formulas (1p-1), (1p-1-2), (1p-2-1), (1p-2-2), (1p-3-1), and (1p-3-2) are preferable, and the repeating units shown by the formulas (1p-1), (1p-2-1), and (1p-3-1) are more preferable.

Specific examples of the repeating units shown by the formulas (1p-1), (1p-2-1), and (1p-3-1) include repeating units shown by the following formulas (1p-1a) to (1p-1-1f), (1p-2-1a) to (1p-2-1f), and (1p-3-1a) to (1p-3-1f), respectively.

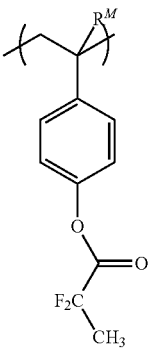
(1p-1-1d)

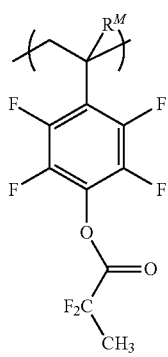
(1p-1-1e)
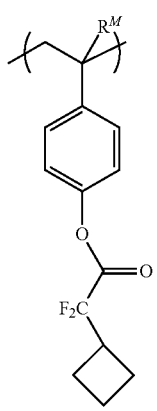
(1p-1-1f)
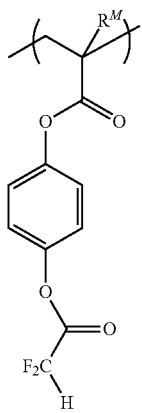
(1p-2-1a)
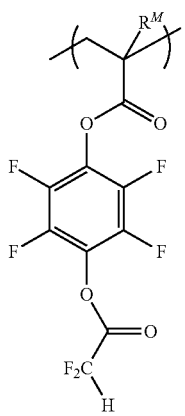
(1p-2-1b)
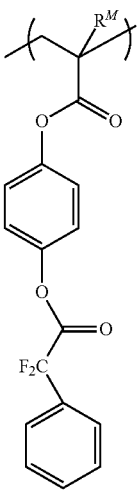
(1p-2-1c)
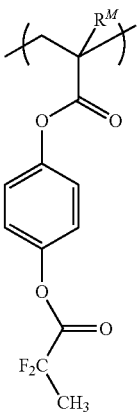
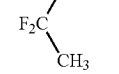
(1p-2-1d)
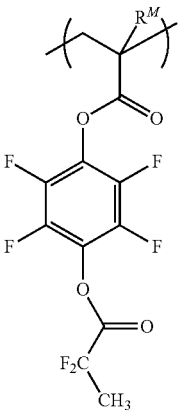
(1p-2-1e)

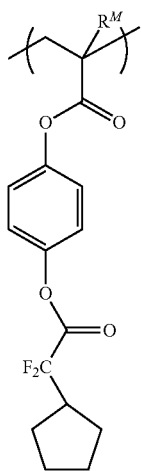 (1p-2-1f)
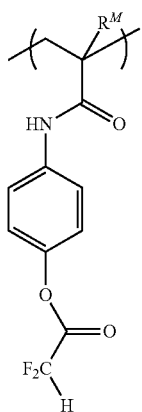 (1p-3-1a)
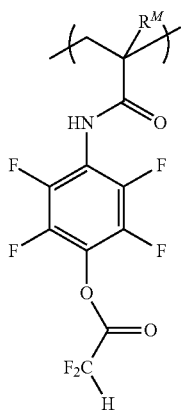 (1p-3-1b)
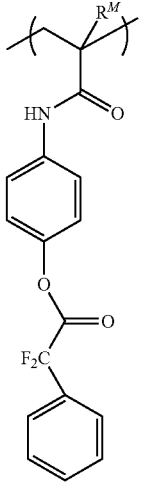 (1p-3-1c)
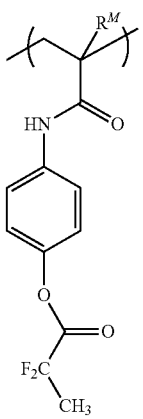 (1p-3-1d)
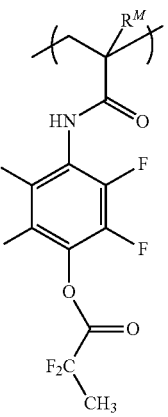 (1p-3-1e)

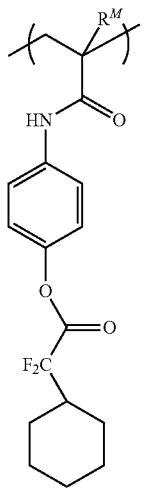

(1p-3-1f)

wherein $R^M$ is the same as defined for the formulas (1m-1-1a) to (1m-3-1f).

When the fluorine-containing compound (A) is a polymer that includes the repeating unit (a1), the content of the repeating unit (a1) in the polymer is preferably 20 to 100 mol %, and more preferably 30 to 100 mol %, based on the total repeating units included in the polymer. If the content of the repeating unit (a1) is within the above range, the surface of the resulting resist film exhibits moderate hydrophobicity during liquid immersion lithography.

When the fluorine-containing compound (A) is a polymer, the fluorine-containing compound (A) may include a repeating unit other than the repeating unit (a1) as long as the effects of the invention are not impaired. The repeating unit other than the repeating unit (a1) is not particularly limited, but is preferably a repeating unit derived from a compound that is copolymerizable with the compound shown by any of the formulas (1m-1) to (1m-3). Repeating units (a2) to (a9) that may be included in the fluorine-containing compound (A) in addition to the repeating unit (a1) are described below. Note that the fluorine-containing compound (A) may be hereinafter referred to as "polymer (A)" when the fluorine-containing compound (A) is a polymer, and may be hereinafter referred to as "low-molecular-weight compound (A)" when the fluorine-containing compound (A) is a low-molecular-weight compound.

<Repeating Unit (a2)>

The polymer (A) may include a repeating unit shown by the following formula (2) (excluding a repeating unit that corresponds to the repeating unit (a1)) as the repeating unit (a2).

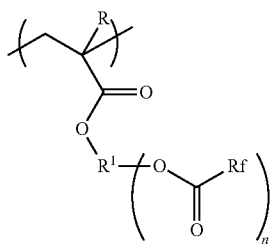

(2)

wherein R represents a hydrogen atom, a fluorine atom, a methyl group, or a trifluoromethyl group, $R^1$ represents an (n+1)-valent linking group, Rf represents a monovalent hydrocarbon group that includes a fluorine atom, and n is an integer from 1 to 3, provided that a plurality of Rf may be either the same or different when n is 2 or 3.

—CO—Rf in the formula (2) functions as an alkali-labile group. Therefore, when the polymer (A) includes the repeating unit (a2), the solubility in an alkaline developer can be improved, and the hydrophobicity of the surface of the resist film after development can be reduced.

Examples of the (n+1)-valent linking group represented by $R^1$ in the formula (2) include a linking group formed by X that represents a single bond or a divalent linking group and $X^1$ that represents an (n+1)-valent linking group. Examples of such a linking group include linking groups shown by the following formulas (X-1) and (X-2).

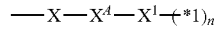  (X-1)

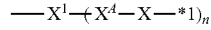  (X-2)

wherein X represents a single bond or a divalent linking group, $X^1$ represents an (n+1)-valent linking group, $X^A$ represents a single bond, an ether group, an ester group, a carbonyl group, an imino group, or an amide group, "*1" indicates a bonding hand, and n is the same as defined for the formula (2), provided that a plurality of $X^A$ and a plurality of X may respectively be either the same or different when n is 2 or 3.

Examples of the divalent linking group represented by X include divalent chain-like hydrocarbon groups having 1 to 30 carbon atoms, divalent alicyclic hydrocarbon groups having 3 to 30 carbon atoms, divalent aromatic hydrocarbon groups having 6 to 30 carbon atoms, and divalent groups formed by any of these groups and an ether group, an ester group, a carbonyl group, an imino group, or an amide group. The divalent linking group may be substituted with a substituent. Specific examples of a substituent that may substitute the divalent linking group include the substituents that may substitute the aromatic ring group represented by $R^C$ in the formula (1).

Examples of the (n+1)-valent linking group represented by $X^1$ include (n+1)-valent chain-like hydrocarbon groups having 1 to 30 carbon atoms, (n+1)-valent alicyclic hydrocarbon groups having 3 to 30 carbon atoms, and (n+1)-valent divalent aromatic hydrocarbon groups having 6 to 30 carbon atoms.

The linking group represented by $X^1$ may be substituted with a substituent. Specific examples of a substituent that may substitute the linking group represented by $X^1$ include the substituents that may substitute the aromatic ring group represented by $R^C$ in the formula (1).

Examples of the monovalent chain-like hydrocarbon group having 1 to 30 carbon atoms that includes a fluorine atom represented by Rf in the formula (2) include groups obtained by substituting 1 to 10 hydrogen atoms of a chain-like hydrocarbon group having 1 to 30 carbon atoms with a fluorine atom.

Examples of the monovalent alicyclic hydrocarbon group having 3 to 30 carbon atoms that includes a fluorine atom represented by Rf in the formula (2) include groups obtained by substituting 1 to 10 hydrogen atoms of an alicyclic hydrocarbon group having 3 to 30 carbon atoms with a fluorine atom.

The group represented by Rf is preferably a perfluoroalkyl group having 1 to 4 carbon atoms, a monoperfluoroalkylmethyl group having 2 to 5 carbon atoms, or a diperfluoroalkylmethyl group having 3 to 5 carbon atoms, and particularly preferably a trifluoromethyl group or a perfluoropropyl group, since the surface of the resulting resist film exhibits a high receding contact angle before development.

Specific examples of the repeating unit (a2) include repeating units shown by the following formulas (2-1) to (2-5).

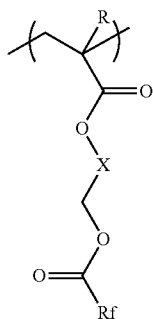
(2-1)

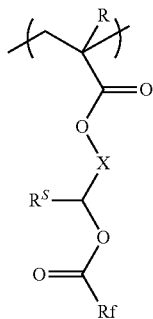
(2-2)

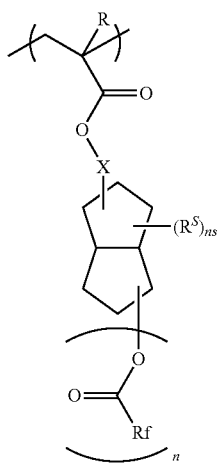
(2-3)

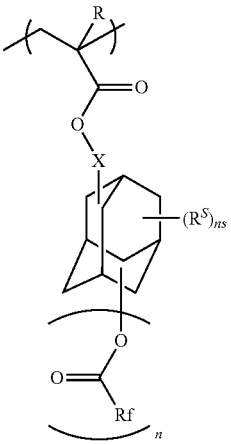
(2-4)

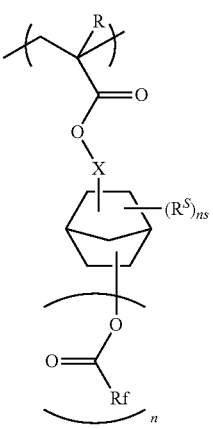
(2-5)

wherein R, X, Rf, and n are the same as defined above, $R^S$ represents $-R^{P3}$, $-R^{P4}-O-R^{P3}$, $-R^{P4}-CO-R^{P3}$, $-R^{P4}-CO-OR^{P3}$, $-R^{P4}-O-CO-R^{P3}$, $-R^{P4}-OH$, $-R^{P4}-CN$, or $-R^{P4}-COOH$ (wherein $R^{P3}$ represents a monovalent chain-like saturated hydrocarbon group having 1 to 10 carbon atoms, a monovalent alicyclic saturated hydrocarbon group having 3 to 20 carbon atoms, or a monovalent aromatic hydrocarbon group having 6 to 30 carbon atoms, provided that some or all of the hydrogen atoms of these groups may be substituted with a fluorine atom, and $R^{P4}$ represents a single bond, a divalent chain-like saturated hydrocarbon group having 1 to 10 carbon atoms, a divalent alicyclic saturated hydrocarbon group having 3 to 20 carbon atoms, a divalent aromatic hydrocarbon group having 6 to 30 carbon atoms, or a group obtained by substituting some or all of the hydrogen atoms of these groups with a fluorine atom), and ns is an integer from 0 to 3, provided that a plurality of $R^S$ may be either the same or different when ns is 2 or 3.

Specific examples of the repeating units shown by the formulas (2-1) to (2-5) include repeating units shown by the following formulas (2p-1) to (2p-7).

(2p-1) 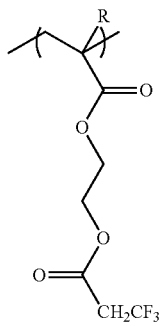

(2p-2) 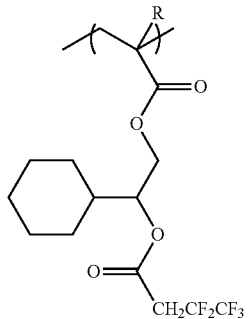

(2p-3) 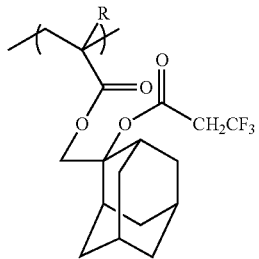

(2p-4) 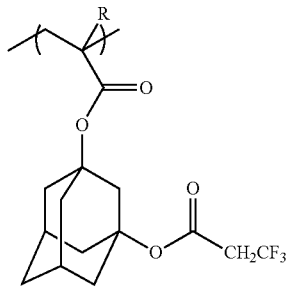

(2p-5) 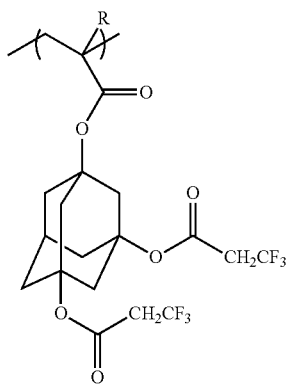

(2p-6) 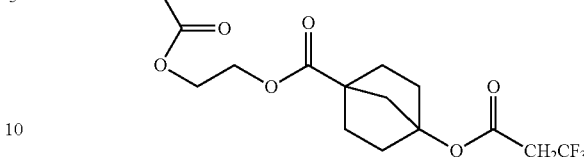

(2p-7)

wherein R is the same as defined for the formula (2-1).

The content of the repeating unit (a2) in the polymer (A) is preferably 0 to 50 mol %, more preferably 0 to 30 mol %, and particularly preferably 0 to 20 mol %, based on the total repeating units included in the polymer (A). The polymer (A) may include only one type of repeating unit (a2), or may include two or more types of repeating unit (a2).

<Repeating Unit (a3)>

The polymer (A) may include a repeating unit shown by the following formula (3) as the repeating unit (a3).

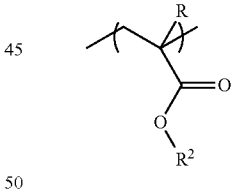

(3)

wherein R represents a hydrogen atom, a fluorine atom, a methyl group, or a trifluoromethyl group, and $R^2$ represents a monovalent hydrocarbon group that includes a fluorine atom.

Specific examples of the monovalent hydrocarbon group represented by $R^2$ in the formula (3) include those mentioned above in connection with Rf in the formula (2). $R^2$ preferably represents a chain-like hydrocarbon group having 1 to 6 carbon atoms that includes a fluorine atom, or an alicyclic hydrocarbon group having 4 to 20 carbon atoms that includes a fluorine atom.

Specific examples of the repeating unit (a3) include the repeating units disclosed in paragraphs [0214] and [0215] of Japanese Patent Application Publication (KOKAI) No. 2007-304537, and repeating units shown by the following formulas.

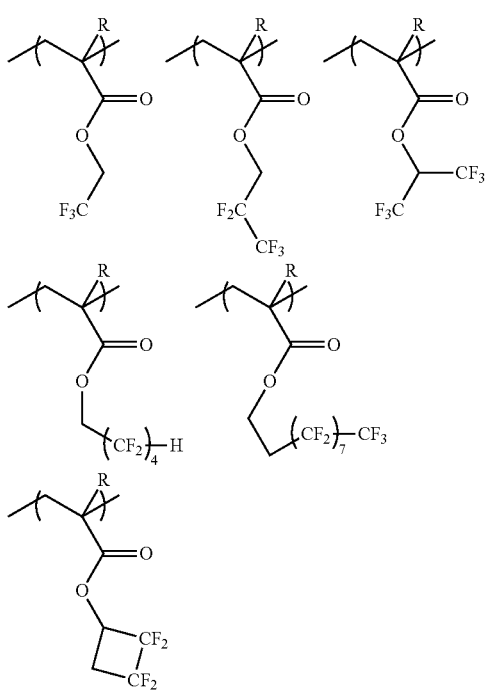

wherein R is the same as defined for the formula (3).

The content of the repeating unit (a3) in the polymer (A) is preferably 0 to 50 mol %, more preferably 0 to 30 mol %, and particularly preferably 0 to 25 mol %, based on the total repeating units included in the polymer (A). The polymer (A) may include only one type of repeating unit (a3), or may include two or more types of repeating unit (a3).

<Repeating Unit (a4)>

The polymer (A) may include a repeating unit shown by the following formula (4) as the repeating unit (a4).

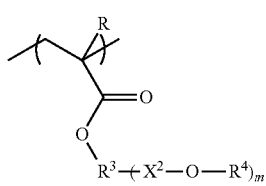
(4)

wherein R represents a hydrogen atom, a fluorine atom, a methyl group, or a trifluoromethyl group, $R^3$ represents an (m+1)-valent linking group, $X^2$ represents a divalent linking group that includes at least one fluorine atom, $R^4$ represents a hydrogen atom or a monovalent organic group, and m is an integer from 1 to 3, provided that a plurality of $X^2$ and a plurality of $R^4$ may respectively be either the same or different when m is 2 or 3.

Specific examples of the linking group represented by $R^3$ in the formula (4) include those mentioned above in connection with le in the formula (2). When the linking group represented by $R^3$ is a hydrocarbon group, an oxygen atom, a sulfur atom, —NR'— (wherein R' represents a hydrogen atom or a monovalent organic group), a carbonyl group, —CO—O—, or —CO—NH— may be bonded to the end of the linking group represented by $R^3$ that is bonded to $X^2$.

When $R^4$ in the formula (4) represents a hydrogen atom, the solubility of the polymer (A) in an alkaline developer can be improved.

Examples of the monovalent organic group represented by $R^4$ in the formula (4) include an acid-labile group, an alkali-labile group, and a substituted or unsubstituted hydrocarbon group having 1 to 30 carbon atoms. When $R^4$ represents an acid-labile group, an area exposed in the exposure step of the method for forming a resist pattern described later exhibits improved solubility in an alkaline developer.

When $R^4$ represents an alkali-labile group, the solubility in an alkaline developer can be improved, and the hydrophobicity of the surface of the resist film after development can be reduced.

Specific examples of the acid-labile group include a t-butoxycarbonyl group, a tetrahydropyranyl group, a tetrahydrofuranyl group, a (thiotetrahydropyranylsulfanyl)methyl group, a (thiotetrahydrofuranylsulfanyl)methyl group, an alkoxy-substituted methyl group, an alkylsulfanyl-substituted methyl group, and the like. Examples of the alkoxy group (substituent) of the alkoxy-substituted methyl group include alkoxy groups having 1 to 4 carbon atoms.

Examples of the alkyl group (substituent) of the alkylsulfanyl-substituted methyl group include alkyl groups having 1 to 4 carbon atoms. Among these, a t-butoxycarbonyl group or an alkoxy-substituted methyl group is preferable.

Specific examples of the alkali-labile group include a group shown by the following formula (W-1).

(W-1)

wherein Rf is the same as defined for the formula (2).

$X^2$ in the formula (4) preferably represents a divalent chain-like hydrocarbon group having 1 to 20 carbon atoms that includes at least one fluorine atom. Specific examples of the divalent chain-like hydrocarbon group represented by $X^2$ include the groups shown by the following formulas (X2-1) to (X2-6).

(X2-1)

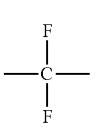
(X2-2)

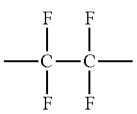
(X2-3)

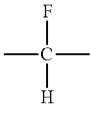
(X2-4)

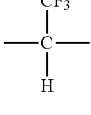
(X2-5)

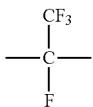
(X2-6)

$X^2$ preferably represents the group shown by the formula (X2-1).

m in the formula (4) is an integer from 1 to 3. Therefore, the repeating unit (a4) includes one, two, or three $R^4$. A plurality of $R^4$ and a plurality of $X^2$ may respectively be either the same or different when m is 2 or 3.

Specifically, a plurality of $R^4$ may have either the same or different structure when m is 2 or 3. When m is 2 or 3, a plurality of $X^2$ may be bonded to an identical carbon atom included in the linking group represented by $R^3$, and may be bonded to different carbon atoms included in the linking group represented by $R^3$.

Specific examples of the repeating unit (a4) include the repeating units disclosed in Japanese Patent Application Publication (KOKAI) No. 2007-204385 (particularly repeating units derived from the monomers described in paragraphs [0240], [0041], [0061], and [0077]).

Specific examples of the repeating unit (a4) are shown below.

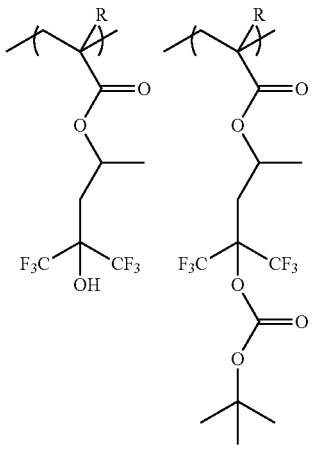

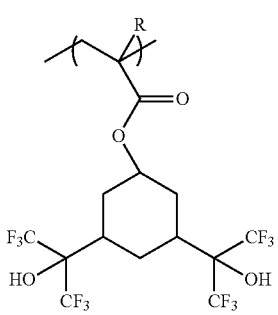

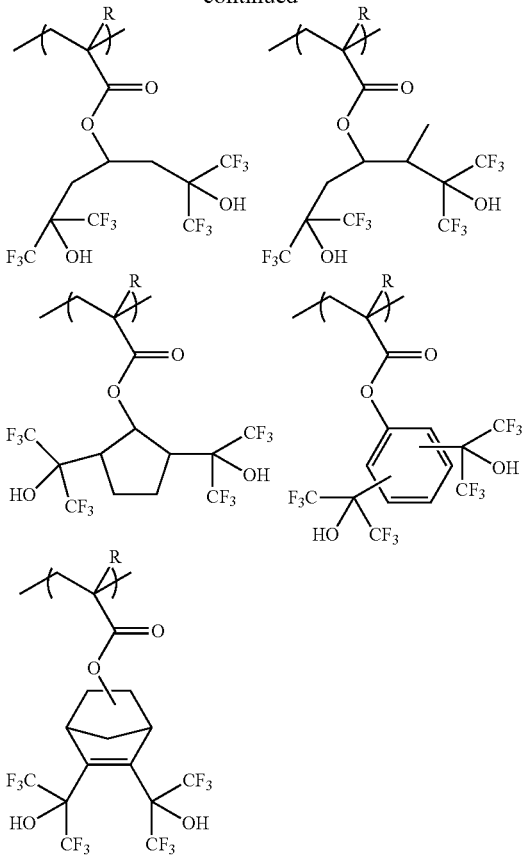

wherein R is the same as defined for the formula (4).

The content of the repeating unit (a4) in the polymer (A) is preferably 0 to 50 mol %, more preferably 5 to 40 mol %, and particularly preferably 0 to 30 mol %, based on the total repeating units included in the polymer (A). The polymer (A) may include only one type of repeating unit (a4), or may include two or more types of repeating unit (a4).

<Repeating Unit (a5)>

The polymer (A) may include a repeating unit shown by the following formula (5) as the repeating unit (a5).

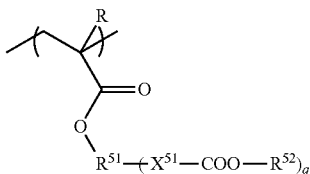

(5)

wherein R represents a hydrogen atom, a fluorine atom, a methyl group, or a trifluoromethyl group, $R^{51}$ represents a (q+1)-valent linking group, $X^{51}$ represents a divalent linking group that includes at least one fluorine atom, $R^{52}$ represents a hydrogen atom or a monovalent organic group, and q is an integer from 1 to 3, provided that a plurality of $X^{51}$ and a plurality of $R^{52}$ may respectively be either the same or different when q is 2 or 3.

Specific examples of the linking group represented by $R^{51}$ in the formula (5) include those mentioned above in connection with $R^3$ in the formula (4).

When $R^{52}$ in the formula (5) represents a hydrogen atom, the solubility of the polymer (A) in an alkaline developer can be improved.

Examples of the monovalent organic group represented by $R^{52}$ include an acid-labile group, an alkali-labile group, and a substituted or unsubstituted hydrocarbon group having 1 to 30 carbon atoms. When $R^{52}$ represents an acid-labile group, an area exposed in the exposure step of the method for forming a resist pattern described later exhibits improved solubility in an alkaline developer. When $R^{52}$ represents an alkali-labile group, the solubility in an alkaline developer can be improved, and the hydrophobicity of the surface of the resist film after development can be reduced. It is preferable that $R^{52}$ represent an alkali-labile group.

Specific examples of the acid-labile group include those mentioned above in connection with $R^4$ in the formula (4). The acid-labile group is preferably a group shown by a formula (Y-1) described later in connection with the repeating unit (a7).

Specific examples of the alkali-labile group include groups shown by the following formulas (Z-1) to (Z-3).

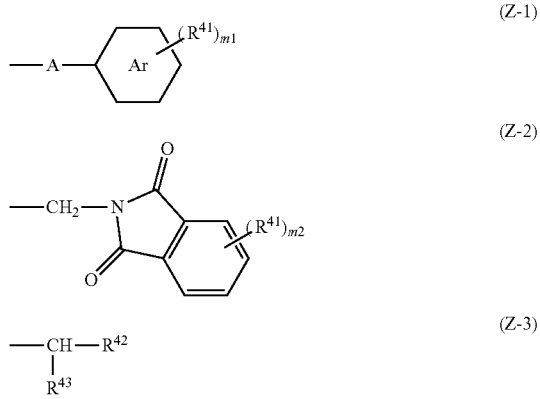

wherein the following symbol represents an aromatic hydrocarbon group,

A represents a single bond or —$CH_2$—, $R^{41}$ represents a substituent, provided that a plurality of $R^{41}$ may be either the same or different when a plurality of $R^{41}$ are present, m1 is an integer from 0 to 5, m2 is an integer from 0 to 4, and $R^{42}$ and $R^{43}$ individually represent a hydrogen atom or an alkyl group having 1 to 10 carbon atoms that may be substituted with a fluorine atom, provided that $R^{42}$ and $R^{43}$ may bond to each other to form an alicyclic hydrocarbon structure having 4 to 20 carbon atoms.

The number of carbon atoms of the ring skeleton of the aromatic hydrocarbon group represented by the following symbol in the formula (Z-1) is preferably 6 to 10. Specific examples of such a ring skeleton include a benzene ring and a naphthalene ring. A benzene ring is preferable from the viewpoint of reactivity.

Examples of the substituent represented by $R^{41}$ in the formulas (Z-1) and (Z-2) include those mentioned above in connection with $R^S$. $R^{41}$ preferably represents a monovalent hydrocarbon group that includes a fluorine atom, or a fluorine atom.

Specific examples of a preferable group shown by the formula (Z-3) include a methyl group, an ethyl group, a 1-propyl group, a 2-propyl group, a 1-butyl group, and a 2-butyl group.

Specific examples of the linking group represented by $X^{51}$ in the formula (5) include those mentioned above in connection with $X^2$ in the formula (4). $X^{52}$ preferably represents a divalent chain-like hydrocarbon group having 1 to 20 carbon atoms that includes at least one fluorine atom, more preferably any of the groups shown by the formulas (X2-2) to (X2-6), and still more preferably the group shown by the formula (X2-2).

q in the formula (5) is an integer from 1 to 3. Therefore, the repeating unit (a5) includes one, two, or three $R^{52}$. A plurality of $R^{52}$ and a plurality of $X^{51}$ may respectively be either the same or different when q is 2 or 3. Specifically, a plurality of $R^{52}$ may have either the same or different structure when q is 2 or 3. When q is 2 or 3, a plurality of $X^{51}$ may be bonded to an identical carbon atom included in the linking group represented by $R^{51}$, and may be bonded to different carbon atoms included in the linking group represented by $R^{51}$.

Specific examples of the repeating unit (a5) include the repeating units disclosed in Japanese Patent Application Publication (KOKAI) No. 2009-019199, the repeating units disclosed in Japanese Patent Application Publication (KOKAI) No. 2009-074085, repeating units shown by the following formulas (5-1a) and (5-1b), and the like.

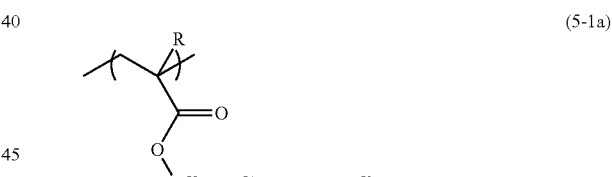

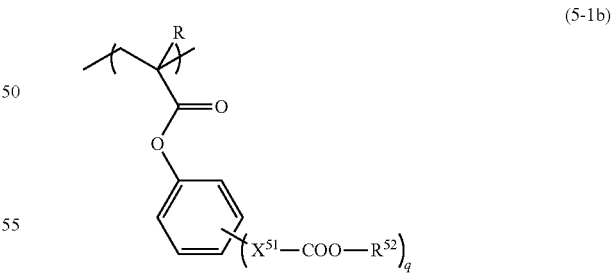

wherein $R^{53}$ represents a divalent linear, branched, or cyclic saturated or unsaturated hydrocarbon group having 1 to 20 carbon atoms, and $X^{51}$, $R^{52}$, and q are the same as defined for the formula (5), provided that a plurality of $X^{51}$ and a plurality of $R^{52}$ may respectively be either the same or different when q is 2 or 3.

Specific examples of the repeating units shown by the formulas (5-1a) and (5-1b) include compounds shown by the following formulas (5p-1) to (5p-7).

(5p-1) 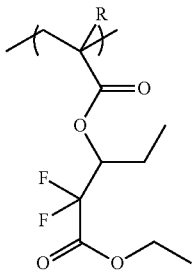

(5p-2) 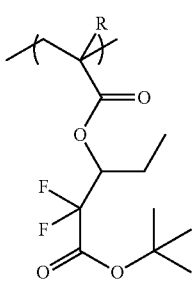

(5p-3) 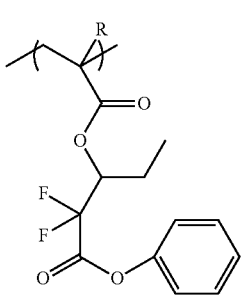

(5p-4) 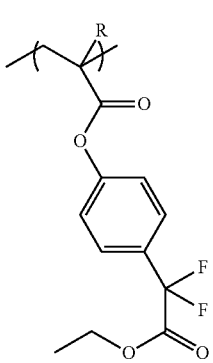

(5p-5) 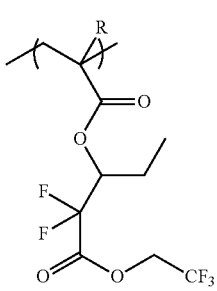

-continued (5p-6) 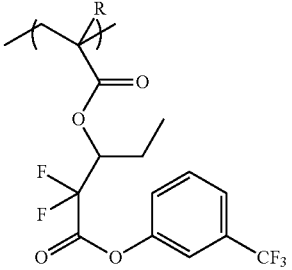

(5p-7) 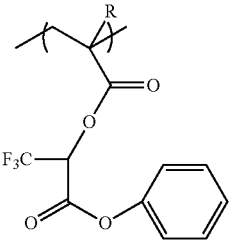

wherein R is the same as defined for the formula (5).

The content of the repeating unit (a5) in the polymer (A) is preferably 0 to 70 mol %, and more preferably 0 to 60 mol %, based on the total repeating units included in the polymer (A). The polymer (A) may include only one type of repeating unit (a5), or may include two or more types of repeating unit (a5).

<Repeating Unit (a6)>

The polymer (A) may include a repeating unit shown by the following formula (6) as the repeating unit (a6).

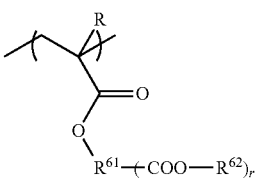

(6)

wherein R represents a hydrogen atom, a fluorine atom, a methyl group, or a trifluoromethyl group, $R^{61}$ represents an (r+1)-valent linking group, $R^{62}$ represents a monovalent hydrocarbon group that includes a fluorine atom, and r is an integer from 1 to 3, provided that a plurality of $R^{62}$ may be either the same or different when r is 2 or 3.

Specific examples of the linking group represented by $R^{61}$ in the formula (6) include those mentioned above in connection with $R^3$ in the formula (4).

Specific examples of the monovalent hydrocarbon group represented by $R^{62}$ in the formula (6) include those mentioned above in connection with Rf in the formula (2). $R^{62}$ preferably represents a chain-like hydrocarbon group having 1 to 6 carbon atoms that includes a fluorine atom, or an alicyclic hydrocarbon group having 4 to 20 carbon atoms that includes a fluorine atom. $R^{62}$ included in the repeating unit (a6) functions as an alkali-labile group. Therefore, when the polymer (A) includes the repeating unit (a6), the solubility in an alkaline developer can be improved, and the hydrophobicity of the surface of the resist film after development can be reduced.

r in the formula (6) is an integer from 1 to 3. Therefore, the repeating unit (a6) includes one, two, or three $R^{62}$. A plurality of $R^{62}$ may be either the same or different when r is 2 or 3.

Specifically, a plurality of $R^{62}$ may have either the same or different structure when r is 2 or 3. When r is 2 or 3, a plurality of —COO—$R^{62}$ may be bonded to an identical carbon atom included in the hydrocarbon group represented by $R^{62}$, or may be bonded to different carbon atoms included in the hydrocarbon group represented by $R^{62}$.

Specific examples of the repeating unit (a6) include the repeating units disclosed in Japanese Patent Application Publication (KOKAI) No. 2010-032994 (particularly (c-1-3) in paragraph [0152], and paragraphs [0155] and [0159] to [0162]), the repeating units disclosed in paragraphs [0063] to [0071] of Japanese Patent Application Publication (KOKAI) No. 20089-111103, repeating units shown by the following formulas (6-1a) and (6-1b), and the ike.

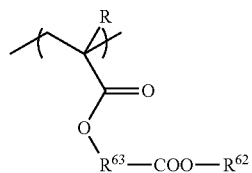

(6-1a)

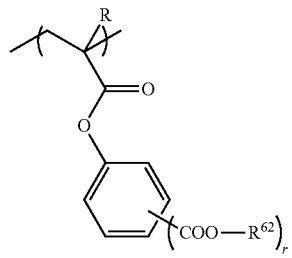

(6-1b)

wherein $R^{63}$ represents a divalent linear, branched, or cyclic saturated or unsaturated hydrocarbon group having 1 to 20 carbon atoms, and $R^{62}$ and r are the same as defined for the formula (6), provided that a plurality of $R^{62}$ may be either the same or different when r is 2 or 3.

Specific examples of the repeating units shown by the formulas (6-1a) and (6-1b) include repeating units shown by the following formulas (6p-1) to (6p-7).

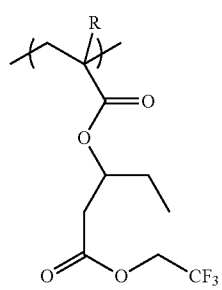

(6p-1)

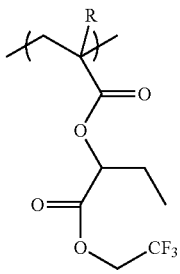

(6p-2)

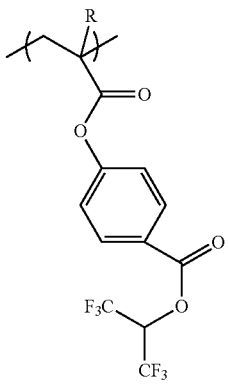

(6p-3)

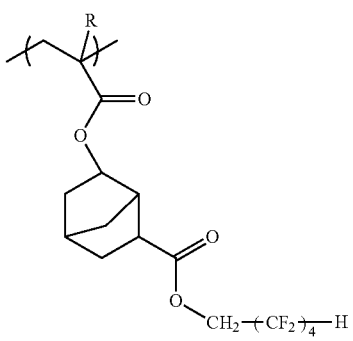

(6p-4)

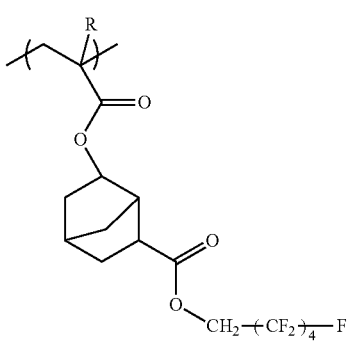

(6p-5)

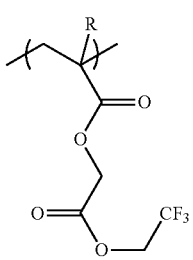

(6p-6)

-continued

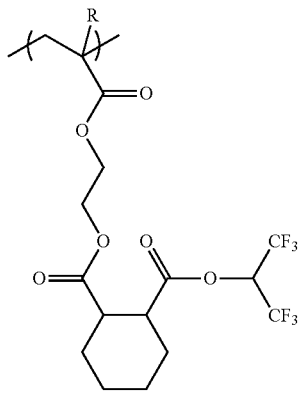

(6p-7)

wherein R is the same as defined for the formula (6).

The content of the repeating unit (a6) in the polymer (A) is preferably 0 to 50 mol %, more preferably 0 to 40 mol %, and particularly preferably 0 to 30 mol %, based on the total repeating units included in the polymer (A). The polymer (A) may include only one type of repeating unit (a6), or may include two or more types of repeating unit (a6).

<Repeating Unit (a7)>

The polymer (A) may include the repeating unit (a7) shown by the following formula (7). If the polymer (A) includes the repeating unit (a7), the shape of the resist pattern after development can be improved.

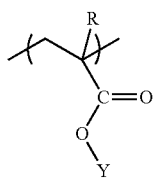

(7)

wherein R represents a hydrogen atom, a methyl group, or a trifluoromethyl group, and Y represents an acid-labile group.

The acid-labile group represented by Y in the formula (7) is preferably a group shown by the following formula (Y-1).

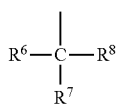

(Y-1)

wherein $R^6$ represents an alkyl group having 1 to 4 carbon atoms or a monovalent alicyclic hydrocarbon group having 4 to 20 carbon atoms, and $R^7$ and $R^8$ individually represent an alkyl group having 1 to 4 carbon atoms or an alicyclic hydrocarbon group having 4 to 20 carbon atoms, or bond to each other to form a divalent alicyclic hydrocarbon group having 4 to 20 carbon atoms together with the carbon atom bonded to $R^7$ and $R^8$.

Examples of the alkyl group having 1 to 4 carbon atoms represented by $R^6$ to $R^8$ in the formula (Y-1) include a methyl group, an ethyl group, an n-propyl group, an i-propyl group, an n-butyl group, a 2-methylpropyl group, a 1-methylpropyl group, a t-butyl group, and the like. Examples of the monovalent alicyclic hydrocarbon group having 4 to 20 carbon atoms or the divalent alicyclic hydrocarbon group having 4 to 20 carbon atoms formed by $R^7$ and $R^8$ together with the carbon atom bonded to $R^7$ and $R^8$ include groups having an alicyclic hydrocarbon skeleton, such as groups having a bridged skeleton (e.g., adamantane skeleton or norbornane skeleton) or a cycloalkane skeleton (e.g., cyclopentane skeleton or cyclohexane skeleton), and groups obtained by substituting these groups with at least one linear, branched, or cyclic alkyl group having 1 to 10 carbon atoms (e.g., methyl group, ethyl group, n-propyl group, or i-propyl group). Among these, a group having a cycloalkane skeleton is preferable since the shape of the resist pattern after development can be further improved.

Specific examples of the repeating unit (a7) include repeating units shown by the following formulas (7-1) to (7-4).

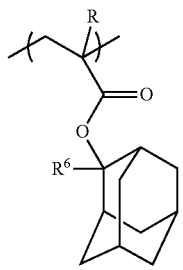

(7-1)

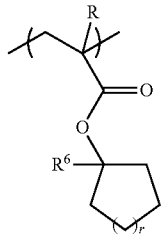

(7-2)

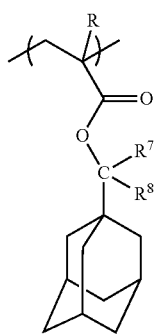

(7-3)

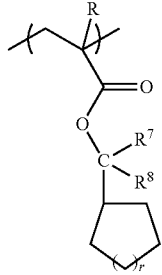

(7-4)

wherein R is the same as defined for the formula (7), $R^6$ to $R^8$ are individually the same as defined for the formula (Y-1), provided that $R^7$ and $R^8$ may bond to each other to form a divalent alicyclic hydrocarbon group having 4 to 20 carbon atoms together with the carbon atom bonded to $R^7$ and $R^8$, and r is an integer from 1 to 3.

The content of the repeating unit (a7) in the polymer (A) is preferably 50 mol % or less, and more preferably 0 to 40 mol %, based on the total repeating units included in the polymer (A). The polymer (A) may include only one type of repeating unit (a7), or may include two or more types of repeating unit (a7).

<Repeating Unit (a8)>

The polymer (A) may include a repeating unit that includes an alkali-soluble group (hereinafter may be referred to as "repeating unit (a8)"). If the polymer (A) includes the repeating unit (a8), affinity to a developer can be improved.

The alkali-soluble group included in the repeating unit (a8) is preferably a functional group that includes a hydrogen atom having a pKa of 4 to 11 from the viewpoint of an improvement in solubility in a developer. Specific examples of such a functional group include functional groups shown by the following formulas (8s-1) and (8s-2), and the like.

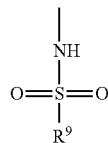

(8s-1)

(8s-2)

wherein $R^9$ represents a hydrocarbon group having 1 to 10 carbon atoms that includes at least one fluorine atom.

The hydrocarbon group having 1 to 10 carbon atoms that includes at least one fluorine atom represented by $R^9$ in the formula (8s-1) is not particularly limited as long as the hydrocarbon group is obtained by substituting some or all of the hydrogen atoms of a hydrocarbon group having 1 to 10 carbon atoms with a fluorine atom. For example, $R^9$ preferably represents a trifluoromethyl group or the like.

A structure for incorporating the repeating unit (a8) in the polymer (A) is not particularly limited, but is preferably a methacrylate structure, an acrylate structure, an α-trifluoroacrylate structure, or the like.

Specific examples of the repeating unit (a8) include repeating units shown by the following formulas (8-1) and (8-2).

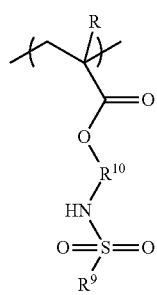

(8-1)

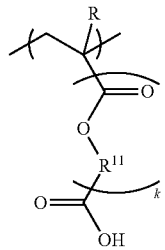

(8-2)

wherein R represents a hydrogen atom, a methyl group, or a trifluoromethyl group, $R^9$ is the same as defined for the formula (8s-1), $R^{10}$ represents a single bond or a divalent linear, branched, or cyclic saturated or unsaturated divalent hydrocarbon group having 1 to 20 carbon atoms, $R^{11}$ represents a divalent linking group, and k is 0 or 1.

Specific examples of the divalent linking group ($R^{11}$) included in the formula (8-2) include those mentioned above in connection with the divalent linking group (X) included in the repeating unit (a2), and the like.

Specific examples of the repeating unit (a8) include repeating units shown by the following formulas (8-1a), (8-1b), and (8-2a) to (8-2e).

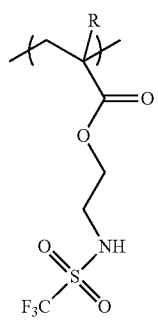

(8-1a)

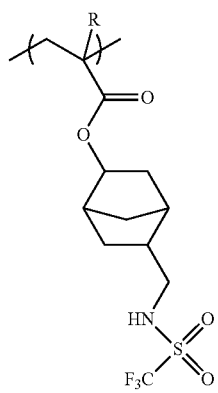

(8-1b)

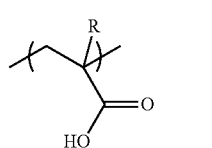

(8-2a)

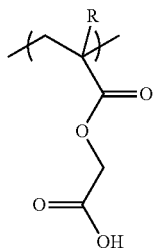

(8-2b)

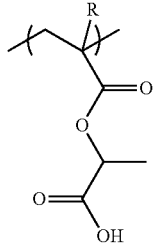

(8-2c)

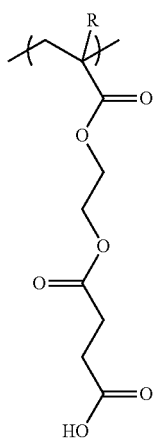

(8-2d)

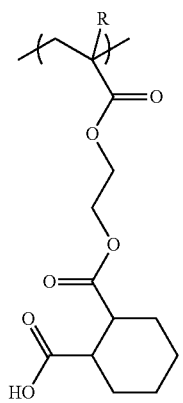

(8-2e)

wherein R represents a hydrogen atom, a methyl group, or a trifluoromethyl group.

The content of the repeating unit (a8) in the polymer (A) is normally 50 mol % or less, preferably 0 to 30 mol %, and more preferably 0 to 20 mol %, based on the total repeating units included in the polymer (A). The polymer (A) may include only one type of repeating unit (a8), or may include two or more types of repeating unit (a8).

<Repeating Unit (a9)>

The polymer (A) may include the repeating unit (a9) shown by the following formula (9).

If the polymer (A) includes the repeating unit (a9), affinity to a developer can be improved.

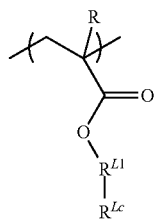

(9)

wherein R represents a hydrogen atom, a methyl group, or a trifluoromethyl group, $R^{L1}$ represents a single bond or a divalent linking group, and $R^{Lc}$ represents a monovalent organic group having a lactone structure or a monovalent organic group having a cyclic carbonate structure.

Specific examples of the divalent linking group ($R^{L1}$) included in the formula (9) include those mentioned above in connection with the divalent linking group (X) included in the repeating unit (a2), and the like.

Specific examples of the monovalent organic group having a lactone structure represented by $R^{Lc}$ in the formula (9) include groups shown by the following formulas (Lc-1) to (Lc-6).

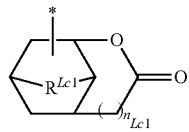

(Lc-1)

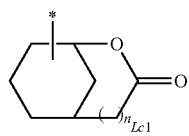

(Lc-2)

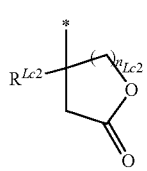

(Lc-3)

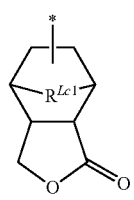

(Lc-4)

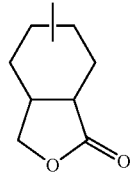

(Lc-5)

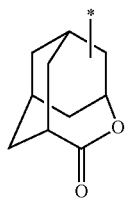
(Lc-6)

wherein $R^{Lc1}$ represents an oxygen atom or a methylene group, $R^{Lc2}$ represents a hydrogen atom or an alkyl group having 1 to 4 carbon atoms, $n_{Lc1}$ is 0 or 1, $n_{Lc2}$ is an integer from 0 to 3, and "*" indicates a bonding hand bonded to $R^{L1}$ in the formula (9). Note that the groups shown by the formulas (Lc-1) to (Lc-6) may be substituted with a substituent.

Examples of a substituent that may substitute the groups shown by the formulas (Lc-1) to (Lc-6) include the substituents mentioned above in connection with $R^C$ in the formula (1).

Specific examples of the repeating unit (a9) include the structural units disclosed in paragraphs [0054] to [0057] of Japanese Patent Application Publication (KOKAI) No. 2007-304537, the structural units disclosed in paragraphs [0086] to [0088] of Japanese Patent Application Publication (KOKAI) No. 2008-088343, and structural units shown by the following formulas (9-1a) to (9-1j).

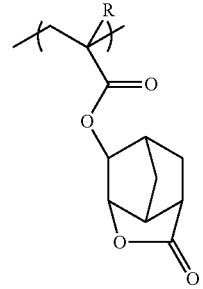
(9-1a)

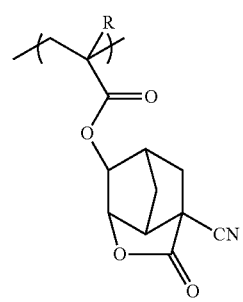
(9-1b)

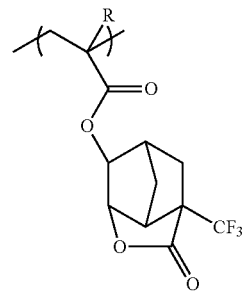
(9-1c)

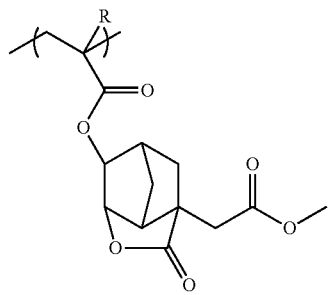
(9-1d)

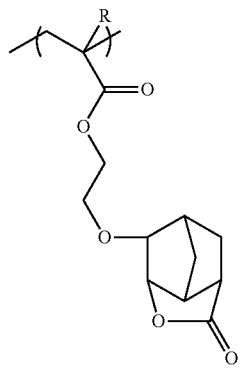
(9-1e)

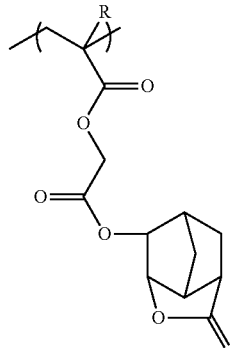
(9-1f)

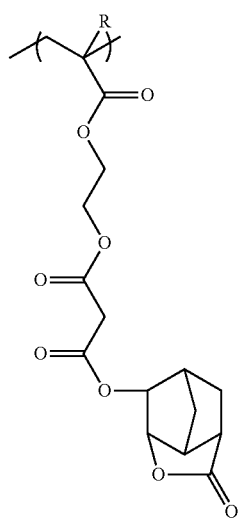
(9-1g)

-continued

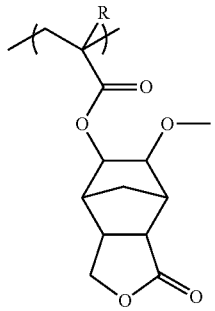
(9-1h)

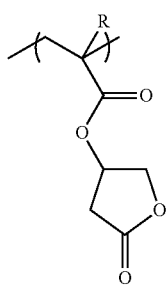
(9-1i)

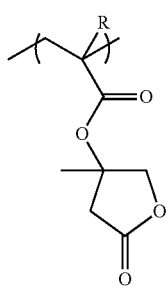
(9-1j)

wherein R represents a hydrogen atom, a methyl group, or a trifluoromethyl group.

The polymer (A) may include only one type of repeating unit (a9), or may include two or more types of repeating unit (a9). Examples of a preferable monomer that produces the repeating unit (a9) include the monomers disclosed in paragraph [0043] of WO2007/116664.

Examples of the repeating unit (a9) having a cyclic carbonate structure include a structural unit shown by the following formula (9-2a).

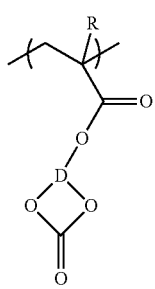
(9-2a)

wherein R is the same as defined for the formula (9), and D represents a trivalent chain-like hydrocarbon group having 1 to 30 carbon atoms, a trivalent alicyclic hydrocarbon group having 3 to 30 carbon atoms, or a trivalent aromatic hydrocarbon group having 6 to 30 carbon atoms. Note that the group represented by D may include an oxygen atom, a carbonyl group, or —NH— in the skeleton, and may be substituted with a substituent.

Examples of a substituent that may substitute the group represented by D include the substituents mentioned above in connection with $R^C$ in the formula (1).

The monomer that produces the repeating unit shown by the formula (9-2a) may be synthesized by the method disclosed in Tetrahedron Letters, Vol. 27, No. 32, p. 3741 (1986), Organic Letters, Vol. 4, No. 15, p. 2561 (2002), or the like.

Examples of a particularly preferable repeating unit shown by the formula (9-2a) include repeating units shown by the following formulas (9-2a-1) to (9-2a-22).

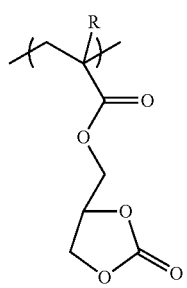
(9-2a-1)

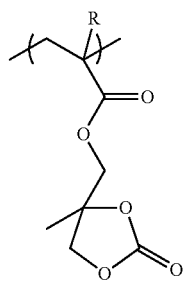
(9-2a-2)

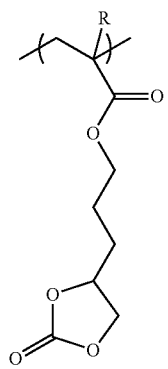
(9-2a-3)

(9-2a-4)
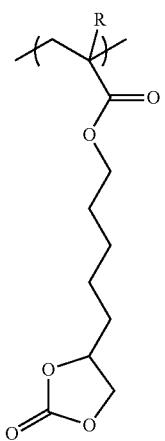
(9-2a-5)
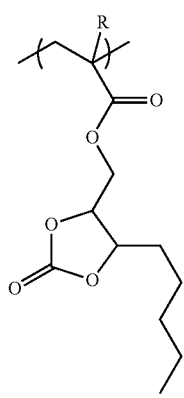
(9-2a-6)
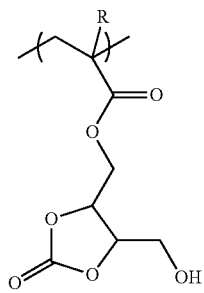
(9-2a-7)
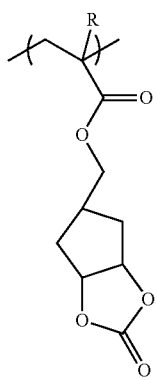
(9-2a-8)
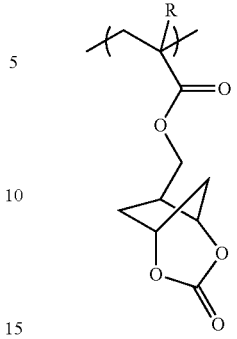
(9-2a-9)
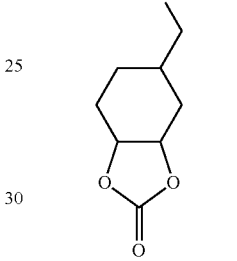
(9-2a-10)
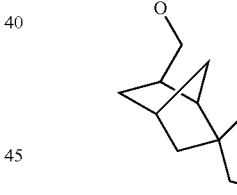
(9-2a-11)
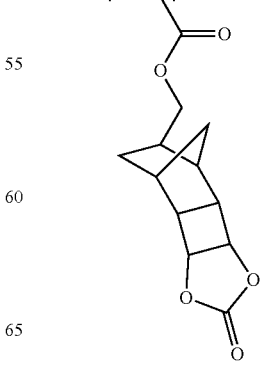

(9-2a-12)
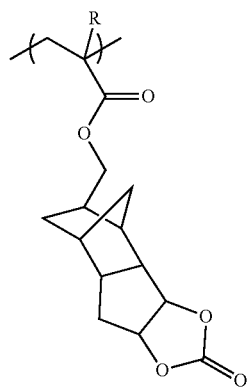
(9-2a-13)
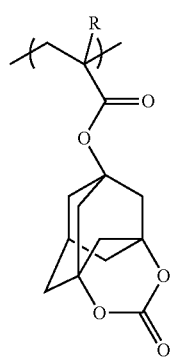
(9-2a-14)
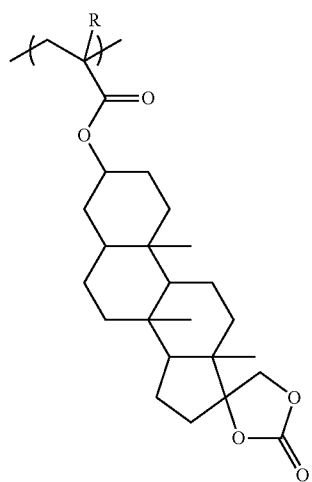
(9-2a-15)
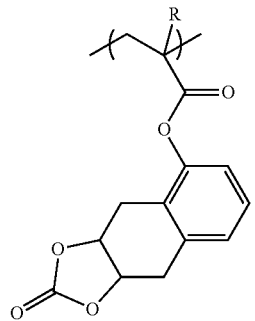
(9-2a-16)
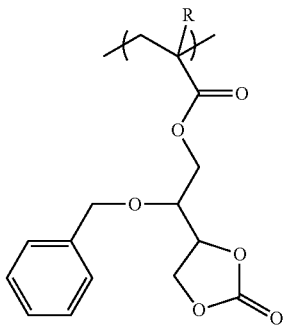
(9-2a-17)
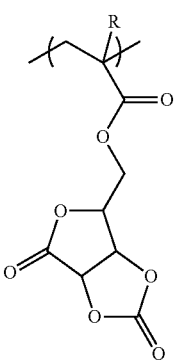
(9-2a-18)
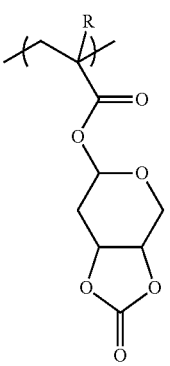
(9-2a-19)
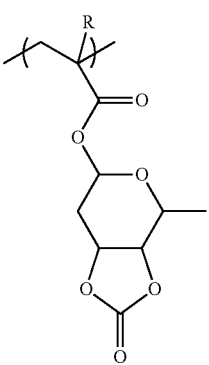

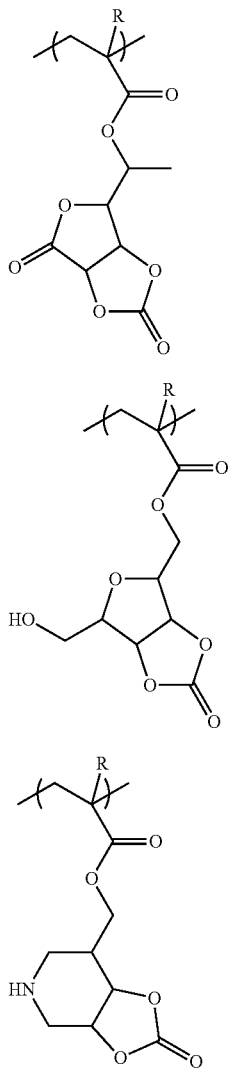

(9-2a-20)

(9-2a-21)

(9-2a-22)

The content of the repeating unit (a9) in the polymer (A) is normally 50 mol % or less, preferably 0 to 40 mol %, and more preferably 0 to 20 mol %, based on the total repeating units included in the polymer (A). The polymer (A) may include only one type of repeating unit (a9), or may include two or more types of repeating unit (a9).

The content of the polymer (A) in the radiation-sensitive resin composition is preferably 0.1 to 20 mass % based on the total amount of the radiation-sensitive resin composition. If the content of the polymer (A) is 0.1 mass % or more, the repeating unit (a1) is uniformly dispersed over the surface of a resist film formed using the composition. As a result, the surface of the resist film exhibits uniform hydrophobicity during liquid immersion lithography, and exhibits uniform surface wettability during alkali development. If the content of the polymer (A) is 20 mass % or less, a pattern can be advantageously formed. The content of the polymer (A) is more preferably 1 to 10 mass %, and still more preferably 3.0 to 8.0 mass %.

The polystyrene-reduced weight average molecular weight (hereinafter may be referred to as "Mw") of the polymer (A) determined by gel permeation chromatography (GPC) is not particularly limited, but is preferably 1000 to 50,000. If the Mw of the polymer (A) is 1000 or more, excellent dry etching resistance is obtained. If the Mw of the polymer (A) is 50,000 or less, the polymer (A) can be easily dissolved in a solvent. The Mw of the polymer (A) is more preferably 2000 to 30,000, and still more preferably 5000 to 15,000.

The ratio (Mw/Mn) of the Mw to the polystyrene-reduced number average molecular weight (hereinafter may be referred to as "Mn") of the polymer (A) determined by GPC is preferably 1.0 to 5.0, more preferably 1.0 to 3.0, and still more preferably 1.0 to 2.0.

The fluorine atom content (mass %) in the polymer (A) is preferably 1 to 40 mass % based on the mass of the polymer (A). If the fluorine atom content is 1 mass % or more, the surface of the resulting resist film exhibits excellent hydrophobicity during liquid immersion lithography. If the fluorine atom content is 40 mass % or less, a pattern can be advantageously formed. The fluorine atom content is more preferably 1.5 to 30 mass %, and still more preferably 2.0 to 20 mass %.

<Method of Producing Low-Molecular-Weight Compound (a)>

When the fluorine-containing compound (A) according to one embodiment of the invention is a low-molecular-weight compound, the low-molecular-weight compound (A) may be produced by reacting a compound that includes a hydrophilic group shown by $—R^C$-QH (wherein $R^C$ and Q are the same as defined above) with a compound that includes a group shown by $—C(=O)—CF_2—R^E$ (wherein $R^E$ is the same as defined above).

The compounds may be reacted by a known method. For example, the low-molecular-weight compound shown by the formula (1) may be produced by reacting a compound (I) shown by the following formula (I) with a compound (II) shown by the following formula (II) so that $—C(=O)—CF_2—R^E$ included in the compound (II) is introduced into the hydrophilic group included in the compound (I).

wherein $R^C$, Q, and $R^E$ are the same as defined for the formula (1), and $X^h$ represents a halogen atom or a hydroxyl group.

Examples of the halogen atom represented by $X^h$ include a bromine atom, a chlorine atom, an iodine atom, a fluorine atom, and the like. Among these, a bromine atom or a chlorine atom is preferable, and a chlorine atom is more preferable, from the viewpoint of reactivity and the like.

The compounds (I) and (II) may be reacted by an arbitrary method. For example, a nucleophilic substitution reaction, a condensation reaction, or the like may be used. When using a nucleophilic substitution reaction, the compounds (I) and (II) are caused to come in contact with each other in a reaction solvent in the presence of a base. When $X^h$ represents a halogen atom, the above reaction may be implemented by adding the compound (II) to a solution of the compound (I) in the presence of a base, for example.

When using a condensation reaction, the above reaction may be implemented by adding the compound (I) to a solution of the compound (II) in the presence of a base and a condensation agent when $X^h$ represents a hydroxyl group, for example. When $X^h$ represents a hydroxyl group, the above reaction may also be implemented by adding the compound (I) to a solution of the compound (II) in the presence of an acid, for example. Note that the compounds (I) and (II) may be obtained by synthesis, or commercially available products may be used as the compounds (I) and (II).

The solvent used for the above reaction is not particularly limited as long as the compounds (I) and (II) can be dissolved. Examples of the solvent include tetrahydrofuran (THF), acetone, dimethylformamide (DMF), dimethylacetamide, dimethyl sulfoxide (DMSO), acetonitrile, dichloromethane, and the like.

Examples of the base include organic bases such as triethylamine, 4-dimethylaminopyridine (DMAP), and pyridine; inorganic bases such as sodium hydride, $K_2CO_3$, and $Cs_2CO_3$; and the like. Examples of the acid include inorganic acids such as hydrochloric acid, sulfuric acid, and phosphoric acid, and organic acids such as methanesulfonic acid, trifluoromethanesulfonic acid, benzenesulfonic acids, and p-toluenesulfonic acid.

Examples of the condensation agent include carbodiimide reagents such as ethyldiisopropylaminocarbodiimide hydrochloride (EDCI), dicyclohexylcarboxylmide (DCC), diisopropylcarbodiimide, and carbodiimidazole, tetraethyl pyrophosphate, benzotriazole-N-hydroxytrisdimethylaminophosphonium hexafluorophosphate (Bop reagent), and the like. These condensation agents may be used either individually or in combination.

The compounds (I) and (II) are preferably used so that the molar ratio of the compound (II) to the compound (I) is 1 to 3, and more preferably 1 to 2.

The reaction temperature may be determined depending on the reaction method and the like, but is preferably −20 to 40° C., and more preferably 0 to 30° C. The reaction time may be determined depending on the reactivity, the reaction temperature, and the like, but is preferably 30 to 240 minutes, and more preferably 45 to 180 minutes. The reaction is preferably carried out in a nitrogen atmosphere.

<Method of Producing Polymer (A)>

The polymer (A) may be synthesized by radical polymerization or the like. For example, the polymer (A) is preferably synthesized by (1) adding a solution containing a monomer and a radical initiator dropwise to a reaction solvent or a solution containing a monomer to effect polymerization, (2) adding a solution containing a monomer and a solution containing a radical initiator dropwise to a reaction solvent or a solution containing a monomer to effect polymerization, or (3) adding a plurality of solutions respectively containing a monomer and a solution containing a radical initiator dropwise to a reaction solvent or a solution containing a monomer to effect polymerization.

When adding a monomer solution dropwise to another monomer solution, the amount of monomer in the monomer solution that is added dropwise to the other monomer solution is preferably 30 mol % or more based on the total amount of monomers subjected to polymerization.

The reaction temperature may be appropriately determined depending on the type of initiator. The reaction temperature is normally 30 to 150° C., preferably 40 to 150° C., and more preferably 50 to 140° C. The dropwise addition time is determined depending on the reaction temperature, the type of initiator, the type of monomer, and the like, but is normally 30 minutes to 8 hours, preferably 45 minutes to 6 hours, and more preferably 1 to 5 hours. The total reaction time including the dropwise addition time is determined depending on the above conditions, but is normally 30 minutes to 12 hours, preferably 45 minutes to 12 hours, and more preferably 1 to 10 hours.

Examples of the radical initiator used for polymerization include azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), dimethyl 2,2'-azobis(2-methylpropionate), and 4,4'-azobis(4-cyanovaleric acid) (V-501); peroxide radical initiators such as benzoyl peroxide, t-butyl hydroperoxide, and cumene hydroperoxide; and the like. These radical initiators may be used either individually or in combination. It is preferable to use AIBN or V-501.

A solvent that is not a solvent that hinders polymerization (e.g., nitrobenzene having a polymerization inhibiting effect or a mercapto compound having a chain transfer effect) and dissolves the monomers may be used as the polymerization solvent. Examples of such a solvent include alcohols, ethers, ketones, amides, ester-lactones, nitriles, a mixed solvent thereof, and the like. These solvents may be used either individually or in combination.

The polymer obtained by polymerization is preferably collected by re-precipitation. Specifically, the polymer solution is poured into a re-precipitation solvent after completion of polymerization to collect the target polymer as a powder. An alcohol, an alkane, and the like may be used as the re-precipitation solvent either individually or in combination. The polymer may also be collected by removing low-molecular-weight components (e.g., monomer and oligomer) by a separation operation, a column operation, ultrafiltration, or the like.

The polymer (A) may also be produced by providing a polymer that includes a hydrophilic group shown by -QH (Q is the same as defined above) (e.g., hydroxystyrene resin or acrylic resin), and introducing a group shown by —C(=O)—$CF_2$—$R^E$ (wherein $R^E$ is the same as defined above) into the hydrophilic group.

<Acid Generator (B)>

Examples of the acid generator (B) included in the radiation-sensitive resin composition according to one embodiment of the invention include onium salt compounds (e.g., sulfonium salts and iodonium salts), organic halogen compounds, and sulfone compounds (e.g., disulfones and diazomethanesulfones). The acid generator (B) may be included in the radiation-sensitive resin composition as a compound (described below) and/or an acid-generating group included in the polymer (A), the polymer (C) (described later), or the like.

Examples of a preferable acid generator (B) include the compounds disclosed in paragraphs [0080] to [0113] of Japanese Patent Application Publication (KOKAI) No. 2009-134088, and the like.

Specific examples of a preferable acid generator (B) include diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, triphenylsulfonium trifluoromethanesulfonate, triphenylsulfonium nonafluoro-n-butanesulfonate, triphenylsulfonium perfluoro-n-octanesulfonate, cyclohexyl•2-oxocyclohexyl•methylsulfonium trifluoromethanesulfonate, dicyclohexyl•2-oxocyclohexylsulfonium trifluoromethanesulfonate, 2-oxocyclohexyldimethylsulfonium trifluoromethanesulfonate, 4-hydroxy-1-naphthyldimethylsulfonium trifluoromethanesulfonate, 4-hydroxy-1-naphthyltetrahydrothiophenium trifluoromethanesulfonate, 4-hydroxy-1-naphthyltetrahydrothiophenium nonafluoro-n-butanesulfonate, 4-hydroxy-1-naphthyltetrahydrothiophenium perfluoro-n-octanesulfonate, 1-(1-naphthylacetomethyl)tetrahydrothiophenium trifluoromethanesulfonate, 1-(1-naphthylacetomethyl)tetrahydrothiophenium nonafluoro-n-butanesulfonate, 1-(1-naphthylacetomethyl)tetrahydrothiophenium perfluoro-n-octanesulfonate, 1-(3,5-dimethyl-4-hydroxyphenyl)tetrahydrothiophenium trifluoromethanesulfonate, 1-(3,5-dimethyl-4-hydroxy phenyl)tetrahydrothiophenium nonafluoro-n-butanesulfonate, 1-(3,5-dimethyl-4-hydroxyphenyl)tetrahydrothiophenium perfluoro-n-octanesulfonate, 4-cyclohexylphenyldiphenylsulfonium perfluoro-n-butanesulfonate, triphenylsulfonium 2-(adamantan-1-yl)-1,1-difluoroethane-1-sulfonate, triphenylsulfonium 6-(adamantan-1-ylcarbonyloxy)-1,1,2,2-tetrafluorohexane-1-sulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimidetrifluoromethanesulfonate, N-hydroxysuccinimidenonafluoro-n-butanesulfonate, N-hydroxysuccinimideperfluoro-n-octanesulfonate, and 1,8-naphthalenedicarboxylic acid imide trifluoromethanesulfonate.

These compounds may be used either individually or in combination as the acid generator (B). The acid generator (B) is preferably used in an amount of 0.1 to 30 parts by mass, and more preferably 0.1 to 20 parts by mass, based on 100 parts by mass of the polymers included in the radiation-sensitive resin composition, so that the resulting resist exhibits excellent sensitivity and developability. If the amount of the acid generator is less than 0.1 parts by mass, a decrease in sensitivity and developability may occur. If the amount of the acid generator exceeds 30 parts by mass, a rectangular resist pattern may not be obtained due to a decrease in transparency to radiation.

<Polymer (C)>

The radiation-sensitive resin composition preferably includes a polymer that includes an acid-labile group in addition to the polymer (A). The polymer that includes an acid-labile group is insoluble or scarcely soluble in alkali, but becomes alkali-soluble upon dissociation (elimination) of the acid-labile group due to an acid generated by the acid generator (B) or the like. The expression "insoluble or scarcely soluble in alkali" means that a film (thickness: 100 nm) that is formed only of the polymer has a thickness equal to or more than 50% of the initial thickness when developed under alkaline conditions employed when forming a resist pattern using a resist film that is formed of the radiation-sensitive resin composition.

When the polymer (A) included in the radiation-sensitive resin composition does not include an acid-labile group, a resist pattern can be formed from a resist film formed using the composition when the composition includes the polymer (C).

It is preferable that the polymer (A) have a fluorine atom content higher than that of the polymer (C). In this case, the polymer (A) tends to be unevenly distributed in the surface layer of a resist film that is formed using the radiation-sensitive resin composition that includes the polymers (A) and (C). Therefore, the group shown by the formula (1) is unevenly distributed in the surface area of the resist film, so that the hydrophobic surface of the resist film promptly becomes hydrophilic during alkali development. This promptly improves the wettability of the surface of the resist film with the developer during alkali development. The fluorine atom content may be determined by $^{13}$C-NMR analysis.

When the polymer (C) does not include a fluorine atom, the polymer (A) preferably has the above fluorine atom content. When the polymer (C) includes a fluorine atom, the ratio of the fluorine atom content of the polymer (A) to the fluorine atom content of the polymer (C) is preferably 1.1 to 3.0. If the ratio of the fluorine atom content of the polymer (A) to the fluorine atom content of the polymer (C) is 1.1 or more, the surface of the resulting resist film exhibits excellent hydrophobicity during liquid immersion lithography. If the ratio of the fluorine atom content of the polymer (A) to the fluorine atom content of the polymer (C) is 3.0 or less, a pattern can be advantageously formed due to excellent dry etching resistance. The ratio of the fluorine atom content of the polymer (A) to the fluorine atom content of the polymer (C) is more preferably 1.2 to 2.5, and still more preferably 1.5 to 2.

The structure of the polymer (C) is not particularly limited as long as the polymer (C) has the above properties. It is preferable that the polymer (C) include the repeating unit (a9) shown by the formula (9). It is also preferable that the polymer (C) further include the repeating unit (a4) shown by the formula (4).

<Repeating Unit (a4)>

The content of the repeating unit (a4) in the polymer (C) is preferably 0 to 30 mol %, and more preferably 0 to 15 mol %, based on the total repeating units included in the polymer (C). If the content of the structural unit (a4) is 30 mol % or less, the resulting pattern rarely peels off due to sufficient adhesion to a substrate.

<Repeating Unit (a9)>

The content of the repeating unit (a9) in the polymer (C) is preferably 5 to 75 mol %, more preferably 15 to 65 mol %, and still more preferably 25 to 55 mol %, based on the total repeating units included in the polymer (C). If the content of the structural unit (a9) is 5 mol % or more, the resulting pattern rarely peels off due to sufficient adhesion to a substrate. If the content of the structural unit (a9) is 75 mol % or less, an excellent pattern shape can be obtained since a decrease in contrast after dissolution rarely occurs.

<Additional Repeating Unit>

The polymer (C) may further include an additional repeating unit other than the repeating units (a4) and (a9) as long as the polymer (C) has the above fluorine atom content. Examples of a polymerizable unsaturated monomer that produces such an additional repeating unit include the monomers disclosed in paragraphs [0065] to [0085] of WO2007/116664A.

A repeating unit derived from 2-hydroxyethyl (meth)acrylate, 2-hydroxypropyl (meth)acrylate, or 3-hydroxypropyl (meth)acrylate is preferable as the additional repeating unit.

The Mw of the polymer (C) is normally 3000 to 300,000, preferably 4000 to 200,000, and still more preferably 4000 to 100,000. If the Mw of the polymer (C) is less than 3000, the heat resistance of the resulting resist may deteriorate. If the Mw of the polymer (C) exceeds 300,000, the developability of the resulting resist may deteriorate.

<Acid Diffusion Controller (D)>

The radiation-sensitive resin composition may optionally include an acid diffusion controller as the component (D). Examples of the acid diffusion controller (D) include compounds shown by the following formula (11) (hereinafter referred to as "nitrogen-containing compounds (I)"), compounds that include two nitrogen atoms in one molecule (hereinafter referred to as "nitrogen-containing compounds (II)"), compounds that include three or more nitrogen atoms in one molecule (hereinafter referred to as "nitrogen-containing compounds (III)"), amide group-containing compounds, urea compounds, nitrogen-containing heterocyclic compounds, and the like. The acid diffusion controller improves the pattern shape and the dimensional accuracy of the resulting resist. The acid diffusion controller (D) may be included in the radiation-sensitive resin composition as a compound (described below) and/or an acid diffusion-controlling group included in the polymer (A), the polymer (C), or the like.

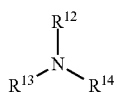
(11)

wherein $R^{12}$ to $R^{14}$ individually represent a hydrogen atom, a substituted or unsubstituted linear, branched, or cyclic alkyl group, an aryl group, or an aralkyl group.

Examples of the nitrogen-containing compound (I) include monoalkylamines such as n-hexylamine; dialkylamines such as di-n-butylamine; trialkylamines such as triethylamine; aromatic amines such as aniline; and the like.

Examples of the nitrogen-containing compound (II) include ethylenediamine, N,N,N',N'-tetramethylethylenediamine, and the like.

Examples of the nitrogen-containing compounds (III) include polyethyleneimine, polyallylamine, poly(dimethylaminoethylacrylamide), and the like.

Examples of the amide group-containing compounds include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compounds include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compounds include pyridines such as pyridine and 2-methylpyridine, pyrazine, pyrazole, and the like.

A compound that includes an acid-labile group may also be used as the nitrogen-containing organic compound.

Examples of the nitrogen-containing organic compound that includes an acid-labile group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl) dicyclohexylamine, N-(t-butoxycarbonyl)diphenylamine, N-(t-butoxycarbonyl)-4-hydroxypiperidine, and the like.

A compound shown by the following formula (12) may also be used as the acid diffusion controller.

$$X^+Z^-$$ (12)

wherein $X^+$ represents a cation shown by the following formula (12-1-1) or (12-1-2), and $Z^-$ represents $OH^-$, an anion shown by $R^{D1}$—$COO^-$, an anion shown by $R^{D1}$—$SO_3^-$, or an anion shown by $R^{D1}$—$N^-$—$SO_2$—$R^{D2}$ (wherein $R^{D1}$ represents a substituted or unsubstituted alkyl group, a substituted or unsubstituted monovalent alicyclic hydrocarbon group, or a substituted or unsubstituted aryl group, and $R^{D2}$ represents an alkyl group in which some or all of the hydrogen atoms are substituted with a fluorine atom, or a monovalent alicyclic hydrocarbon group).

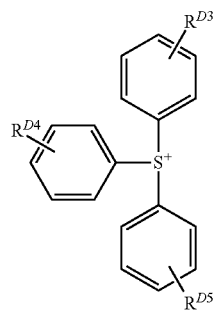
(12-1-1)

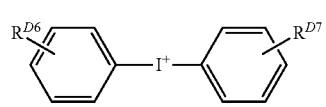
(12-1-2)

wherein $R^{D3}$ to $R^{D5}$ individually represent a hydrogen atom, an alkyl group, an alkoxy group, a hydroxyl group, or a halogen atom, and $R^{D6}$ and $R^{D7}$ individually represent a hydrogen atom, an alkyl group, an alkoxy group, a hydroxyl group, or a halogen atom.

The above compound is used as an acid diffusion controller that loses acid diffusion controllability upon decomposition due to exposure (hereinafter may be referred to as "photodegradable acid diffusion controller"). The above compound allows diffusion of an acid in the exposed area, but controls diffusion of an acid in the unexposed area, so that the contrast between the exposed area and the unexposed area is improved (i.e., the boundary between the exposed area and the unexposed area becomes distinct). This is effective for reducing the line width roughness (LWR) and the mask error enhancement factor (MEEF) of the radiation-sensitive resin composition.

$X^+$ in the formula (12) represents the cation shown by the formula (12-1-1) or (12-1-2). $R^{D3}$ to $R^{D5}$ in the formula (12-1-1) individually represent a hydrogen atom, an alkyl group, an alkoxy group, a hydroxyl group, or a halogen atom. $R^{D3}$ to $R^{D5}$ preferably represent a hydrogen atom, an alkyl group, an alkoxy group, or a halogen atom since the solubility of the compound in a developer decreases. $R^{D6}$ and $R^{D7}$ in the formula (12-1-2) individually represent a hydrogen atom, an alkyl group, an alkoxy group, a hydroxyl group, or a halogen atom. $R^{D6}$ and $R^{D7}$ preferably represent a hydrogen atom, an alkyl group, or a halogen atom.

$Z^-$ in the formula (12) represents $OH^-$, an anion shown by $R^{D1}$—$COO^-$, an anion shown by $R^{D1}$—$SO_3^-$, or an anion shown by $R^{D1}$—$N^-$—$SO_2$—$R^{D2}$. $R^{D1}$ represents a substituted or unsubstituted alkyl group, a substituted or unsubstituted alicyclic hydrocarbon group, or a substituted or unsubstituted aryl group. $R^{D1}$ preferably represents an alicyclic hydrocarbon group or an aryl group since the solubility of the compound in a developer decreases.

Examples of the substituted or unsubstituted alkyl group represented by $R^{D1}$ include groups that include one or more substituents such as hydroxyalkyl groups having 1 to 4 carbon atoms such as a hydroxymethyl group; alkoxy groups having 1 to 4 carbon atoms such as a methoxy group; a cyano group; and cyanoalkyl groups having 2 to 5 carbon atoms such as a cyanomethyl group. Among these, a hydroxymethyl group, a cyano group, and a cyanomethyl group are preferable.

Examples of the substituted or unsubstituted alicyclic hydrocarbon group represented by $R^{D1}$ include monovalent groups derived from an alicyclic hydrocarbon such as a cycloalkane skeleton (e.g., hydroxycyclopentane, hydroxycyclohexane, or cyclohexanone), or a bridged alicyclic hydrocarbon skeleton (e.g., 1,7,7-trimethylbicyclo[2.2.1]heptan-2-one (camphor)). Among these, a group derived from 1,7,7-trimethylbicyclo[2.2.1]heptan-2-one is preferable.

Examples of the substituted or unsubstituted aryl group represented by $R^{D1}$ include a phenyl group, a benzyl group, a phenylethyl group, a phenylpropyl group, a phenylcyclohexyl group, and groups obtained by substituting these groups (compounds) with a hydroxyl group, a cyano group, or the like. Among these, a phenyl group, a benzyl group, and a phenylcyclohexyl group are preferable.

$Z^-$ in the formula (12) preferably represents the anion shown by the following formula (12-2-1) (i.e., an anion shown by $R^{D1}$—COO$^-$ wherein $R^{D1}$ represents a phenyl group), the anion shown by the following formula (12-2-2) (i.e., an anion shown by $R^{D1}$—SO$_3^-$ wherein $R^{D1}$ represents a group derived from 1,7,7-trimethylbicyclo[2.2.1]heptan-2-one), or the anion shown by the following formula (12-2-3) (i.e., an anion shown by $R^{D1}$—N$^-$—SO$_2$—$R^{D2}$ wherein $R^{D1}$ represents a butyl group, and $R^{D2}$ represents a trifluoromethyl group).

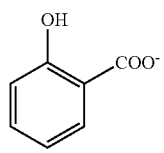

(12-2-1)

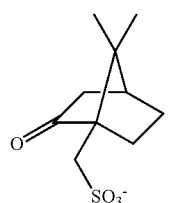

(12-2-2)

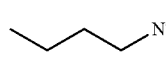

(12-2-3)

The photodegradable acid diffusion controller is shown by the general formula (12). Specifically, the photodegradable acid diffusion controller is a sulfonium salt compound or an iodonium salt compound that satisfies the above conditions.

Examples of the sulfonium salt compounds include triphenylsulfonium hydroxide, triphenylsulfonium salicylate, triphenylsulfonium 4-trifluoromethyl salicylate, diphenyl-4-hydroxyphenylsulfonium salicylate, triphenylsulfonium 10-camphorsulfonate, 4-t-butoxyphenyl·diphenylsulfonium 10-camphorsulfonate, and the like.

These sulfonium salt compounds may be used either individually or in combination.

Examples of the iodonium salt compounds include bis(4-t-butylphenyl)iodonium hydroxide, bis(4-t-butylphenyl)iodonium salicylate, bis(4-t-butylphenyl)iodonium 4-trifluoromethyl salicylate, bis(4-t-butylphenyl)iodonium 10-camphorsulfonate, and the like. These iodonium salt compounds may be used either individually or in combination.

These acid diffusion controllers (D) may be used either individually or in combination. The acid diffusion controller (D) is preferably used in an amount of 10 parts by mass or less, and more preferably 5 parts by mass or less, based on 100 parts by mass of the polymers included in the radiation-sensitive resin composition.

If the amount of the acid diffusion controller (D) is too large, the sensitivity of the resulting resist film may unduly decrease.

<Solvent (E)>

The radiation-sensitive resin composition according to one embodiment of the invention normally includes a solvent. The solvent is not particularly limited as long as at least the polymer (A), the acid generator (B), the optional polymer (C), and the like can be dissolved therein. Examples of the solvent (E) include linear or branched ketones, cyclic ketones, propylene glycol monoalkyl ether acetates, alkyl 2-hydroxypropionates, alkyl 3-alkoxypropionates, and the like.

Among these, linear or branched ketones, cyclic ketones, propylene glycol monoalkyl ether acetates, alkyl 2-hydroxypropionates, alkyl 3-alkoxypropionates, and the like are preferable, and propylene glycol monomethyl ether acetate and cyclohexanone are more preferable. These solvents may be used either individually or in combination.

<Additive (F)>

The radiation-sensitive resin composition according to one embodiment of the invention may optionally include an uneven distribution promoter, a surfactant, an alicyclic compound, a sensitizer, a crosslinking agent, and the like as the additive (F).

(Uneven Distribution Promoter)

The uneven distribution promoter causes the polymer (A) to be more efficiently unevenly distributed over the surface of the resist film. The amount of the polymer (A) used to produce the radiation-sensitive resin composition can be reduced by adding the uneven distribution promoter to the radiation-sensitive resin composition. This makes it possible to further suppress elution of components from the resist film to an immersion liquid, or implement high-speed liquid immersion lithography via a high-speed scan without impairing the basic resist performance (e.g., LWR, development defect resistance, and pattern collapse resistance), so that the hydrophobicity of the surface of the resist film that suppresses defects (e.g., watermark defects) that may occur due to liquid immersion lithography can be improved. Examples of the uneven distribution promoter include a low-molecular-weight compound having a relative dielectric constant of 30 to 200 and a boiling point at 1 atmosphere of 100° C. or more. Examples of such a compound include lactone compounds, carbonate compounds, nitrile compounds, polyhydric alcohols, and the like.

Specific examples of lactone compounds include γ-butyrolactone, valerolactone, mevalonic lactone, norbornane lactone, and the like.

Specific examples of carbonate compounds include propylene carbonate, ethylene carbonate, butylene carbonate, vinylene carbonate, and the like.

Specific examples of nitrile compounds include succinonitrile and the like. Specific examples of polyhydric alcohols include glycerol and the like.

The uneven distribution promoter is added to the radiation-sensitive resin composition according to one embodiment of the invention in an amount of 10 to 500 parts by mass, and preferably 30 to 300 parts by mass, based on 100 parts by mass of the polymers. These uneven distribution promoters may be used either individually or in combination.

(Surfactant)

The surfactant improves the applicability, the developability, and the like of the radiation-sensitive resin composition. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate, commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination. The surfactant is normally used in an amount of 2 parts by mass or less based on 100 parts by mass of the polymers included in the radiation-sensitive resin composition.

(Alicyclic Skeleton-Containing Compound)

The alicyclic skeleton-containing compound further improves the dry etching resistance, the pattern shape, adhesion to a substrate, and the like. Examples of the alicyclic skeleton-containing compound include adamantane derivatives such as 1-adamantanecarboxylic acid, 2-adamantanone, and t-butyl 1-adamantanecarboxylate; deoxycholates such as t-butyl deoxycholate, t-butoxycarbonylmethyl deoxycholate, and 2-ethoxyethyl deoxycholate; lithocholates such as t-butyl lithocholate, t-butoxycarbonylmethyl lithocholate, and 2-ethoxyethyl lithocholate; 3-[2-hydroxy-2,2-bis(trifluoromethyl)ethyl]tetracyclo[4.4.0.1$^{2,5}$.1$^{7,10}$]dodecane; 2-hydroxy-9-methoxycarbonyl-5-oxo-4-oxa-tricyclo[4.2.1.0$^{3,7}$]nonane; and the like. These alicyclic skeleton-containing compounds may be used either individually or in combination. The alicyclic skeleton-containing compound is normally used in an amount of 50 parts by mass or less, and preferably 30 parts by mass or less, based on 100 parts by mass of the polymers included in the radiation-sensitive resin composition.

(Sensitizer)

The sensitizer absorbs energy other than the energy of radiation absorbed by the acid generator (B), and transmits the energy to the acid generator (B) as radicals to increase the amount of acid generated. The sensitizer thus improves the apparent sensitivity of the radiation-sensitive resin composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination.

(Crosslinking Agent)

When using the radiation-sensitive resin composition according to one embodiment of the invention as a negative-tone radiation-sensitive resin composition, the radiation-sensitive resin composition may include a compound (hereinafter referred to as "crosslinking agent") that crosslinks an alkaline developer-soluble polymer in the presence of an acid. Examples of the crosslinking agent include a compound that includes at least one functional group (hereinafter referred to as "crosslinkable functional group") that exhibits crosslinking reactivity with an alkaline developer-soluble polymer.

Examples of the crosslinkable functional group include a glycidyl ether group, a glycidyl ester group, a glycidyl amino group, a methoxymethyl group, an ethoxymethyl group, a benzyloxymethyl group, an acetoxymethyl group, a benzoiloxymethyl group, a formyl group, an acetyl group, a vinyl group, an isopropenyl group, a (dimethylamino)methyl group, a (diethylamino)methyl group, a (dimethylolamino)methyl group, a (diethylolamino)methyl group, a morpholinomethyl group, and the like.

Examples of the crosslinking agent include the crosslinking agents disclosed in paragraphs [0169] to [0172] of WO2009/51088.

A methoxymethyl group-containing compound (e.g., dimethoxymethylurea or tetramethoxy methyl glycoluril) is particularly preferable as the crosslinking agent. The negative-tone radiation-sensitive resin composition may include only one type of crosslinking agent, or may include two or more types of crosslinking agent.

The crosslinking agent is preferably used in an amount of 5 to 95 parts by mass, more preferably 15 to 85 parts by mass, and particularly preferably 20 to 75 parts by mass, based on 100 parts by mass of the alkaline developer-soluble polymer. If the amount of the crosslinking agent is less than 5 parts by mass, the residual ratio may decrease, or the resulting pattern may be curved or may swell, for example. If the amount of the crosslinking agent exceeds 95 parts by mass, the alkali developability of the composition may deteriorate.

A dye, a pigment, an adhesion improver, and the like may also be used as the additive (F). For example, a dye or a pigment visualizes the latent image in the exposed area, and reduces the effect of halation during exposure. An adhesion improver improves adhesion to a substrate. Examples of other additives include an alkali-soluble resin, a low-molecular-weight alkali-solubility controller that includes an acid-labile protecting group, a halation inhibitor, a preservation stabilizer, an anti-foaming agent, and the like.

These additives (F) may be used either individually or in combination.

<Production of Radiation-Sensitive Resin Composition Solution>

The radiation-sensitive resin composition according to one embodiment of the invention is normally prepared as a composition solution by dissolving the components in the solvent so that the total solid content is 1 to 50 mass %, and preferably 3 to 25 mass %, and filtering the solution through a filter having a pore size of about 0.2 μm, for example.

It is preferable that the radiation-sensitive resin composition have an impurity (e.g., halogen ions and metals) content as low as possible. The sensitivity, the resolution, the process stability, the pattern shape, and the like of the resist film can be further improved by reducing the impurity content. Therefore, the fluorine-containing compound (A) and the polymer (C) used to produce the radiation-sensitive resin composition is preferably purified by chemical purification (e.g., washing with water or liquid-liquid extraction) or a combination of chemical purification and physical purification (e.g., ultrafiltration or centrifugation).

<Method for Forming Photoresist Pattern>

A method for forming a resist pattern according to one embodiment of the invention includes (1) forming a photoresist film on a substrate using the radiation-sensitive resin composition (hereinafter may be referred to as "step (1)"), (2) providing an immersion liquid over the photoresist film, and subjecting the photoresist film to liquid immersion lithography via the immersion liquid (hereinafter may be referred to as "step (2)"), and (3) developing the photoresist film subjected to liquid immersion lithography to form a resist pattern (hereinafter may be referred to as "step (3)"). The above method makes it possible to form a resist pattern having an excellent pattern shape.

In the step (1), a photoresist film is formed by applying the radiation-sensitive composition solution according to one embodiment of the invention to a substrate (e.g., silicon wafer or aluminum-coated wafer) by an appropriate coating method (e.g., rotational coating, cast coating, or roll coating). Specifically, the radiation-sensitive resin composition solution is applied so that the resulting resist film has a given thickness, and prebaked (PB) to volatilize the solvent from the film. A resist film is thus formed.

The thickness of the resist film is not particularly limited, but is preferably 10 to 5000 nm, and more preferably 10 to 2000 nm.

The prebaking temperature is determined depending on the composition of the radiation-sensitive resin composition, but is preferably about 30 to 200° C., and more preferably 50 to 150° C.

In the step (2), radiation is applied to the photoresist film formed by the step (1) via an immersion liquid provided over the photoresist film (i.e., the photoresist film is subjected to liquid immersion lithography).

Purified water, a long-chain or cyclic aliphatic compound, or the like may be used as the immersion liquid.

Visible rays, ultraviolet rays, deep ultraviolet rays, X-rays, electron beams, or the like may be appropriately used as the radiation depending on the type of acid generator. It is preferable to use deep ultraviolet rays such as ArF excimer laser light (wavelength: 193 nm) or KrF excimer laser light (wavelength: 248 nm). It is particularly preferable to use ArF excimer laser light (wavelength: 193 nm).

The exposure conditions (e.g., dose) may be appropriately selected depending on the composition of the radiation-sensitive resin composition, the type of additive, and the like.

It is preferable to perform post-exposure bake (PEB). The acid-labile group included in the resin component dissociates smoothly due to PEB. The PEB temperature may be appropriately adjusted depending on the composition of the radiation-sensitive resin composition, but is normally 30 to 200° C., and preferably 50 to 170° C.

In order to maximize the performance of the radiation-sensitive resin composition, an organic or inorganic antireflective film may be formed on the substrate, as disclosed in Japanese Examined Patent Publication (KOKOKU) No. 6-12452 (Japanese Patent Application Publication (KOKAI) No. 59-93448), for example. A protective film may be formed on the photoresist film (see Japanese Patent Application Publication (KOKAI) No. 5-188598, for example) in order to prevent an adverse effect of basic impurities and the like contained in the environmental atmosphere. In order to prevent outflow of the acid generator and the like from the photoresist film during liquid immersion lithography, a liquid immersion lithography protective film may be formed on the photoresist film, as disclosed in Japanese Patent Application Publication (KOKAI) No. 2005-352384, for example. These techniques may be used in combination.

When using the method for forming a resist pattern that utilizes liquid immersion lithography, a resist pattern can be formed only of the photoresist film obtained using the radiation-sensitive resin composition according to one embodiment of the invention without forming a protective film (upper-layer film) on the photoresist film. In this case, the throughput is expected to be improved since it is unnecessary to form a protective film (upper-layer film).

In the step (3), the resist film subjected to liquid immersion lithography is developed to form a given resist pattern.

It is preferable to use an alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water as the developer.

The concentration of the alkaline aqueous solution is preferably 10 mass % or less. If the concentration of the alkaline aqueous solution exceeds 10 mass %, the unexposed area may be dissolved in the developer.

An organic solvent may be added to the alkaline aqueous solution (developer).

Examples of the organic solvent include ketones such as acetone, methyl ethyl ketone, methyl i-butyl ketone, cyclopentanone, cyclohexanone, 3-methylcyclopentanone, and 2,6-dimethylcyclohexanone, alcohols such as methyl alcohol, ethyl alcohol, n-propyl alcohol, i-propyl alcohol, n-butyl alcohol, t-butyl alcohol, cyclopentanol, cyclohexanol, 1,4-hexanediol, and 1,4-hexanedimethylol, ethers such as tetrahydrofuran and dioxane, esters such as ethyl acetate, n-butyl acetate, and i-amyl acetate, aromatic hydrocarbons such as toluene and xylene, phenol, acetonylacetone, dimethylformamide, and the like.

These organic solvents may be used either individually or in combination.

The organic solvent is preferably used in an amount of 100 parts by volume or less based on 100 parts by volume of the alkaline aqueous solution. If the amount of the organic solvent exceeds 100 parts by volume, the exposed area may remain undeveloped due to a decrease in developability.

An appropriate amount of a surfactant or the like may also be added to the alkaline aqueous solution (developer).

After development using the alkaline aqueous solution (developer), the resist film is normally rinsed with water, and dried.

The radiation-sensitive resin composition according to one embodiment of the invention includes the fluorine-containing compound (A) that includes the group shown by the formula (1). Since the fluorine-containing compound (A) includes a fluorine-substituted hydrocarbon group, the fluorine-containing compound (A) exhibits high hydrophobicity. Therefore, the surface of the resist film formed on a substrate exhibits a high receding contact angle during liquid immersion lithography.

The low-molecular-weight compound (A) or the polymer (A) that includes at least the repeating unit (a1) may be used as the fluorine-containing compound (A). If the radiation-sensitive resin composition includes the polymer (A) that has a fluorine atom content higher than that of the polymer (C), the fluorine-containing compound (A) is highly distributed in the surface of the resulting resist film. As a result, elution of the acid generator and the like from the resist film can be suppressed, and the surface of the resist film exhibits an excellent draining capability.

In the fluorine-containing compound (A), the fluorine atoms are bonded to the carbon atom present at the $\alpha$ position with respect to the carbonyl group. Therefore, the carbon atom of the carbonyl group exhibits high reactivity, so that the group —$CO$—$CF_2$—$R_E$ dissociates promptly under alkaline conditions to produce a hydrophilic group (-QH). The fluorine-containing compound (A) thus exhibits a high rate of reaction with an alkaline developer as compared with a compound in which the fluorine atoms are bonded to the carbon atom present at the $\beta$ position with respect to the carbonyl group. Therefore, when forming a resist film using the composition that includes the fluorine-containing compound (A), the surface of the resist film exhibits hydrophobicity due to the fluorine atom included in the fluorine-containing compound (A), and a hydrophilic group (-QH) is promptly produced when the resist film is subjected to alkaline conditions, so that the surface of the resist film promptly changes from a hydrophobic surface to a hydrophilic surface. As a result, impurities (e.g., development residue) rarely adhere to the surface of the film during alkali development. Moreover, since the alkaline developer is promptly spread over the surface of the resist film when the alkaline developer has come in contact with the surface of the resist film, the resist film can be advantageously developed. Therefore, the composition according to one embodiment of the invention makes it possible to form a resist film that can suppress occurrence of development defects as much as possible.

<Evaluation of Rate of Reaction>

The rate of reaction (rate of hydrolysis) of the fluorine-containing compound (A) with the alkaline developer may be evaluated using the contact angle with water (e.g., static contact angle (i.e., the contact angle of the resist film in a horizontal state with a water droplet) or dynamic contact angle (i.e., the contact angle of the resist film in a tilted state with a water droplet)) or the like as an index. The rate of hydrolysis may be evaluated by causing a resist film that includes the fluorine-containing compound (A) to come in contact with the alkaline developer, and measuring a change in contact angle with time after causing the resist film to come in contact with the alkaline developer.

It is preferable to use the dynamic contact angle (e.g., sliding angle, advancing contact angle, or receding contact angle), and it is more preferable to use the receding contact angle. The term "sliding angle" refers to the contact angle when a water droplet has moved, and the term "advancing contact angle" refers to the contact angle with the resist film at the front endpoint in the moving direction of a water droplet. The term "receding contact angle" refers to the contact angle with the resist film at the rear endpoint in the moving direction of a water droplet. The advancing contact angle and the receding contact angle increase and the sliding angle decreases as the hydrophobicity of the resist film increases. Specifically, a decrease in advancing contact angle and receding contact angle increases and an increase in sliding angle increases as the rate of reaction of the fluorine-containing compound (A) with the alkaline developer increases.

The invention is further described below by way of examples. Note that the invention is not limited to the following examples. The property values were measured by the following methods.

[Weight Average Molecular Weight (Mw) and Number Average Molecular Weight (Mn)]

The weight average molecular weight (Mw) and the number average molecular weight (Mn) were measured by gel permeation chromatography (GPC) using GPC columns manufactured by Tosoh Corporation (G2000HXL×2, G3000HXL×1, G4000HXL×1) at a flow rate of 1.0 ml/min and a column temperature of 40° C. (eluant: tetrahydrofuran, standard: monodisperse polystyrene).

[$^1$H-NMR Analysis and $^{13}$C-NMR Analysis]

The $^1$H-NMR analysis of the compound and the $^{13}$C-NMR analysis for determining the fluorine atom content of the polymer were performed using a nuclear magnetic resonance spectrometer ("JNM-ECX400" manufactured by JEOL Ltd.).

<Synthesis of Compound>

[Example 1]

A solution prepared by dissolving 13.3 g (0.069 mol) of difluoroacetic acid in 60 ml of dichloromethane was slowly added to 60 ml of a dichloromethane solution of 27 g (0.066 mol) of dicyclohexylcarbodiimide (DCC), 0.37 g (0.003 mol) of dimethylaminopyridine (DMAP), and 10.7 g (0.06 mol) of p-hydroxyphenyl methacrylate at 0° C. in a nitrogen atmosphere. The mixture was allowed to return to room temperature, and stirred for 1 hour. After the addition of 200 g of purified water and 30 g of diatomaceous earth to the reaction mixture, the mixture was filtered under reduced pressure. The filtrate was separated using a separating funnel, and the organic layer was washed three times with purified water. After evaporating the solvent from the organic layer using an evaporator, the resulting crude product was dissolved in hexane heated at 40° C. The solution was cooled to 0° C. to precipitate a white solid. The white solid was collected by filtration. 6.9 g of a compound (M-1) shown by the following formula was thus obtained as a white solid (yield: 45%).

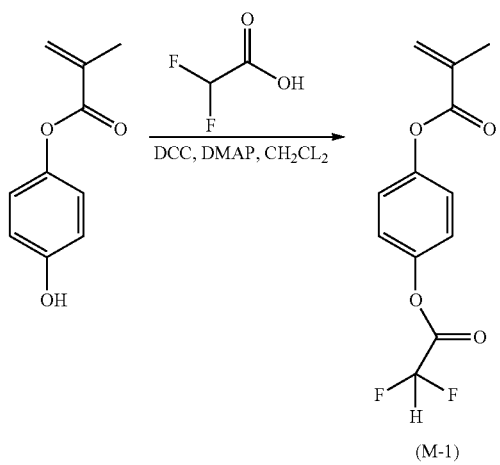

(M-1)

The compound (M-1) was subjected to $^1$H-NMR analysis (400 MHz). The results are shown below.

$^1$H-NMR (solvent: CDCl$_3$): 7.6-7.1 (m, 4H), 6.40 (s, 1H), 5.80 (s, 1H), 5.2-5.6 (m, 1H), 2.10 (s, 3H).

It was thus confirmed that the compound (M-1) had the following structure.

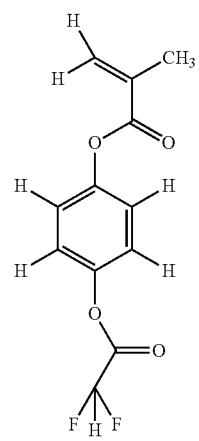

[Comparative Synthesis Example 1]

A solution prepared by dissolving 9.0 g (0.069 mol) of 3,3,3-trifluoropropionic acid in 60 ml of dichloromethane was slowly added to 60 ml of a dichloromethane solution of 27 g (0.066 mol) of dicyclohexylcarbodiimide (DCC), 0.37 g (0.003 mol) of dimethylaminopyridine (DMAP), and 10.7 g (0.06 mol) of p-hydroxyphenyl methacrylate at 0° C. in a nitrogen atmosphere. The mixture was allowed to return to room temperature, and stirred for 1 hour. After the addition of 200 g of purified water and 30 g of diatomaceous earth to the reaction mixture, the mixture was filtered under reduced pressure. The filtrate was separated using a separating funnel, and the organic layer was washed three times with purified water. After evaporating the solvent from the organic layer using an evaporator, the resulting crude product was dissolved in hexane heated at 40° C. The solution was cooled to 0° C. to precipitate a white solid. The white solid was collected by filtration. 8.7 g of a compound (M-2) shown by the following formula was thus obtained as a white solid (yield: 50%).

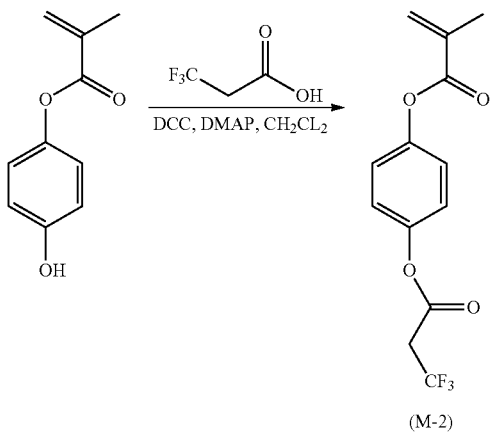

The compound (M-2) was subjected to $^1$H-NMR analysis (400 MHz). The results are shown below.

$^1$H-NMR (solvent: CDCl$_3$): 7.6-7.1 (m, 4H), 6.35 (s, 1H), 5.80 (s, 1H), 4.0-4.3 (m, 2H), 2.05 (s, 3H).

It was thus confirmed that the compound (M-2) had the following structure.

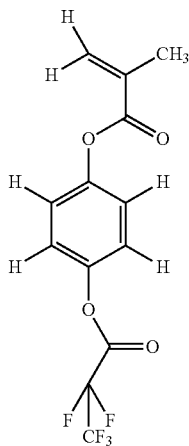 [SMILES: C=C(C)C(=O)Oc1ccc(OC(=O)C(F)(F)C(F)(F)F)cc1]

<Synthesis of Polymer (A)>

Polymers (A-1) to (A-6) (polymer (A)) were synthesized by the following method using the compound (M-1) and a compound selected from compounds (M-4), (M-7), (M-10), and (M-13) shown by the following formulas. As comparative examples, a polymer (A'-1) was synthesized by the following method using the compound (M-2), and a polymer (A'-2) was synthesized by the following method without using the compounds (M-1) and (M-2).

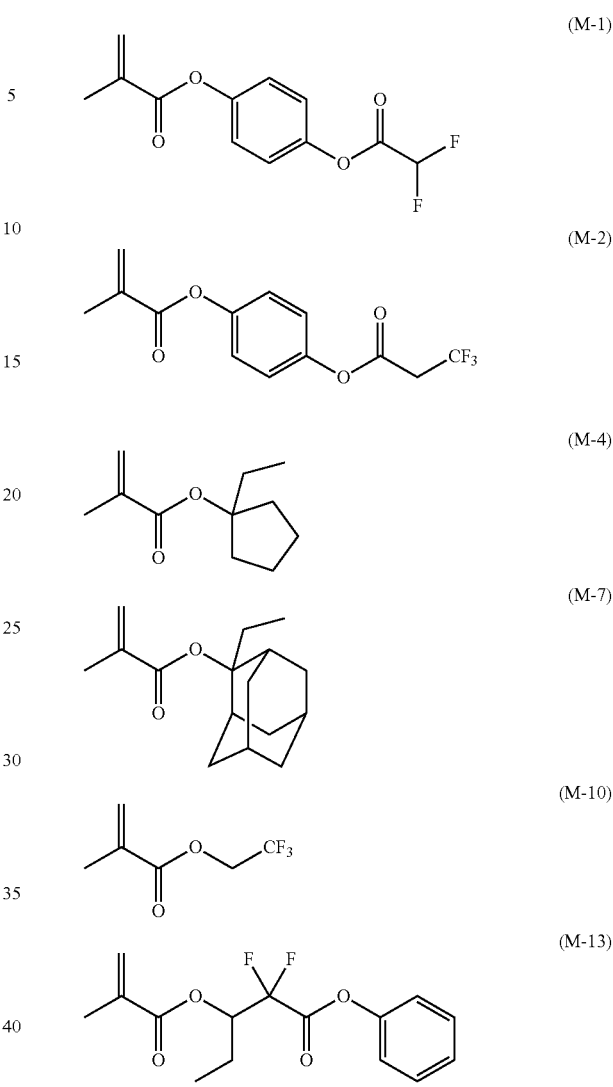

[Example 2]

A three-necked flask equipped with a thermometer and a reflux condenser was charged with 9.03 g (0.0352 mol) of the compound (M-1) synthesized in Example 1, 0.97 g (0.0039 mol) of the compound (M-7), and 20 g of methyl ethyl ketone. The mixture was stirred to dissolve the compounds. 0.32 g (1.96 mmol) of azobisisobutyronitrile (initiator) (manufactured by Wako Pure Chemical Industries, Ltd.) was added to (dissolved in) the solution. The resulting solution was heated at 80° C. for 5 hours with stirring to effect polymerization. The reaction mixture was then cooled to room temperature. The reaction mixture was concentrated under reduced pressure, and slowly added to 150 g of n-hexane. A solid that precipitated by this operation was washed three times with hexane, and dried under reduced pressure to obtain a solid. The solid was subjected to $^{13}$C-NMR analysis (400 MHz). It was found that the ratio of t1 to t2 in the following formula was 91.8:8.2 (molar ratio). The solid had a fluorine atom content of 6.28 mass %. The polystyrene-reduced mass average molecular weight and the dispersity of the solid determined by GPC were 8900 and 1.52, respectively. This polymer is referred to as "polymer (A-1)".

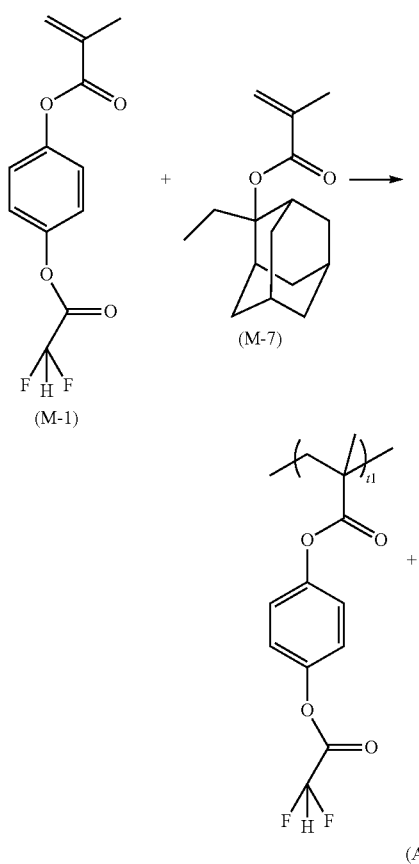

(M-1)

(M-7)

(M-2)

(A-1)

[Comparative Example 1]

A three-necked flask equipped with a thermometer and a reflux condenser was charged with 9.34 g (0.032 mol) of the compound (M-2) synthesized in Comparative Synthesis Example 1, 0.65 g (0.0036 mol) of the compound (M-4), and 20 g of methyl ethyl ketone. The mixture was stirred to dissolve the compounds. 0.47 g (2.88 mmol) of azobisisobutyronitrile (initiator) (manufactured by Wako Pure Chemical Industries, Ltd.) was added to (dissolved in) the solution. The resulting solution was heated at 80° C. for 5 hours with stirring to effect polymerization. The reaction mixture was then cooled to room temperature. The reaction mixture was concentrated under reduced pressure, and slowly added to 150 g of n-hexane. A solid that precipitated by this operation was washed three times with hexane, and dried under reduced pressure to obtain a solid. The solid was subjected to $^{13}$C-NMR analysis (400 MHz). It was found that the ratio of t3 to t4 in the following formula was 89.7:10.3 (molar ratio). The polystyrene-reduced mass average molecular weight and the dispersity of the solid determined by GPC were 9300 and 1.60, respectively. This polymer is referred to as "polymer (A'-1)".

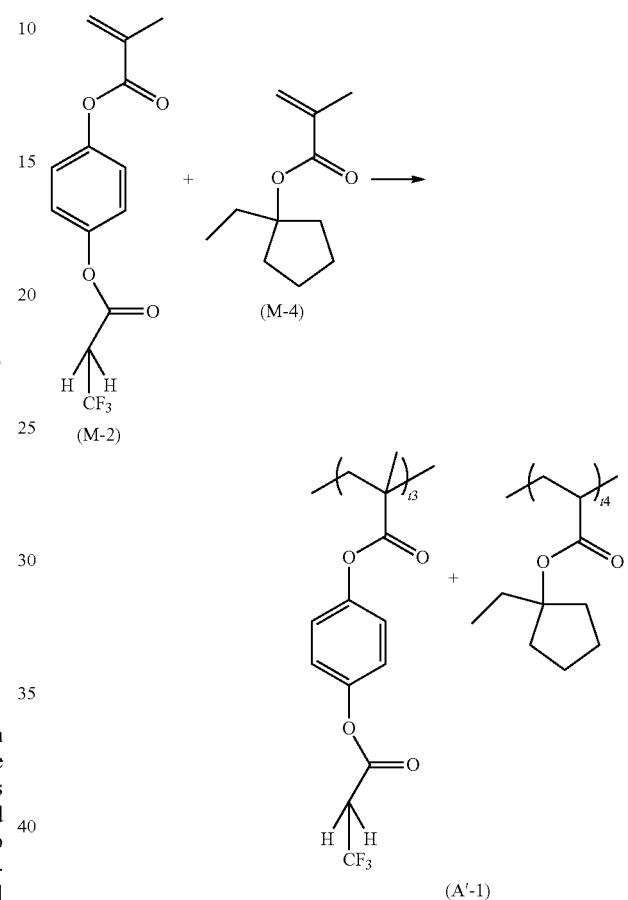

(M-4)

(A'-1)

[Examples 3 to 7 and Comparative Example 2]

The polymers (A-2) to (A-6) and (A'-2) were synthesized in the same manner as in Example 2, except for using the compounds shown in Table 1. The property values of each polymer are also shown in Table 1.

TABLE 1

| Polymer (A) | | Compound | | Structural unit in polymer | Property value | | |
|---|---|---|---|---|---|---|---|
| | | Type | Amount (mol %) | Content (mol %) | Mw | Mw/Mn | Fluorine atom content (mass %) |
| Example 3 | (A-1) | M-7 | 10 | 8.2 | 8900 | 1.52 | 6.28 |
| | | M-1 | 90 | 91.8 | | | |
| Example 4 | (A-2) | M-4 | 10 | 9.9 | 11,500 | 1.55 | 6.10 |
| | | M-1 | 90 | 90.1 | | | |
| Example 5 | (A-3) | M-1 | 100 | 100.0 | 8900 | 1.40 | 7.14 |
| Example 6 | (A-4) | M-4 | 50 | 51.5 | 8800 | 1.50 | 2.69 |
| | | M-1 | 50 | 48.5 | | | |
| Example 7 | (A-5) | M-4 | 10 | 10.2 | 9900 | 1.49 | 7.86 |
| | | M-10 | 20 | 20.2 | | | |
| | | M-1 | 70 | 69.6 | | | |

TABLE 1-continued

| Polymer (A) | | Compound | | Structural unit in polymer | Property value | | |
|---|---|---|---|---|---|---|---|
| | | Type | Amount (mol %) | Content (mol %) | Mw | Mw/Mn | Fluorine atom content (mass %) |
| Example 8 | (A-6) | M-4 | 10 | 10.4 | 12,000 | 1.55 | 5.10 |
| | | M-13 | 60 | 59.1 | | | |
| | | M-1 | 30 | 30.5 | | | |
| Comparative Example 1 | (A'-1) | M-4 | 10 | 10.3 | 9300 | 1.60 | 8.19 |
| | | M-2 | 90 | 89.7 | | | |
| Comparative Example 2 | (A'-2) | M-4 | 70 | 69.9 | 7000 | 1.41 | 3.55 |
| | | M-10 | 30 | 30.1 | | | |

<Synthesis of Polymer (C)>

Polymers (C-1) and (C-2) were synthesized by the following method.

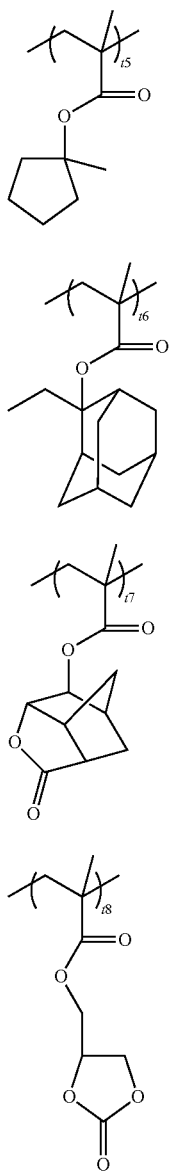

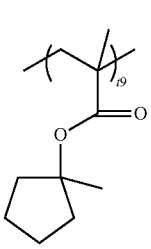

(M-3)

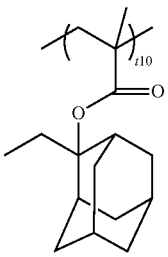

(M-7)

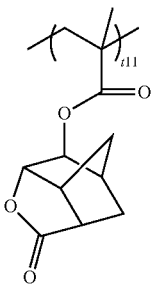

(M-8)

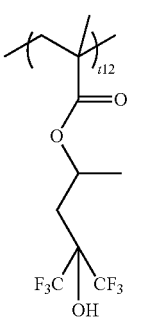

(M-12)

[Synthesis Example 1]

86.61 g (0.515 mol) of the compound (M-3), 68.65 g (0.309 mol) of the compound (M-8), and 19.17 g (0.103 mol) of the compound (M-11) were dissolved in 400 g of 2-butanone, and 8.45 g of dimethyl 2,2'-azobis(2-isobutylonitrile) was added to the solution to prepare a monomer solution. A three-necked flask (2000 ml) was charged with 25.57 g (0.103 mol) of the compound (M-7). 200 g of 2-butanone was added to the flask to dissolve the compound. The flask was then purged with nitrogen for 30 minutes, and heated to 80° C. with stirring. The monomer solution was added dropwise to the flask using a dropping funnel over 3 hours. The compounds were polymerized for 6 hours from the start of addition of the monomer solution. After completion of polymerization, the polymer solution was cooled with water to 30° C. or less, and poured into 4000 g of methanol. A white powder that precipitated by this operation was collected by filtration. The white powder thus collected was washed with methanol in a slurry state, and collected by filtration. This operation was repeated once. The powder was then dried at 60° C. for 15 hours to obtain a white powdery copolymer (C-1) (150.6 g, yield: 75.3%). The copolymer (C-1) had an Mw of 6700 and a ratio Mw/Mn of 1.47. As a result of $^{13}$C-NMR analysis, it was found that the ratio of the content (mol %) of a repeating unit derived from the compound (M-3), the content (mol %) of a repeating unit derived from the compound (M-7), the content (mol %) of a repeating unit derived from the compound (M-8), and the content (mol %) of a repeating unit derived from the compound (M-11) was 49.0:9.2:31.6:10.1.

[Synthesis Example 2]

86.61 g (0.515 mol) of the compound (M-3), 68.65 g (0.309 mol) of the compound (M-8), and 30.39 g (0.103 mol) of the compound (M-12) were dissolved in 400 g of 2-butanone, and 8.45 g of dimethyl 2,2'-azobis(2-isobutylonitrile) was added to the solution to prepare a monomer solution. A three-necked flask (2000 ml) was charged with 25.57 g (0.103 mol) of the compound (M-7). 200 g of 2-butanone was added to the flask to dissolve the compound. The flask was then purged with nitrogen for 30 minutes, and heated to 80° C. with stirring. The monomer solution was added dropwise to the flask using a dropping funnel over 3 hours. The compounds were polymerized for 6 hours from the start of addition of the monomer solution. After completion of polymerization, the polymer solution was cooled with water to 30° C. or less, and poured into 4000 g of methanol. A white powder that precipitated by this operation was collected by filtration. The white powder thus collected was washed with methanol in a slurry state, and collected by filtration. This operation was repeated once. The powder was then dried at 60° C. for 15 hours to obtain a white powdery copolymer (C-2) (131 g, yield: 65.5%). The copolymer (C-2) had an Mw of 5500 and a ratio Mw/Mn of 1.401. As a result of $^{13}$C-NMR analysis, it was found that the ratio of the content (mol %) of a repeating unit derived from the compound (M-3), the content (mol %) of a repeating unit derived from the compound (M-7), the content (mol %) of a repeating unit derived from the compound (M-8), and the content (mol %) of a repeating unit derived from the compound (M-12) was 51.7:8.3:30.8:9.2. The copolymer (C-2) had a fluorine atom content of 3.56 mass %.

<Production of Radiation-Sensitive Resin Composition>

Components (acid generator (B) and acid diffusion controller (D)) of the radiation-sensitive resin composition other than the polymers (A-1) to (A-6), (A'-1), (A'-2), (C-1), and (C-2) synthesized in the examples and the comparative examples are shown below.

Acid generator (B): compounds shown by the following formulas

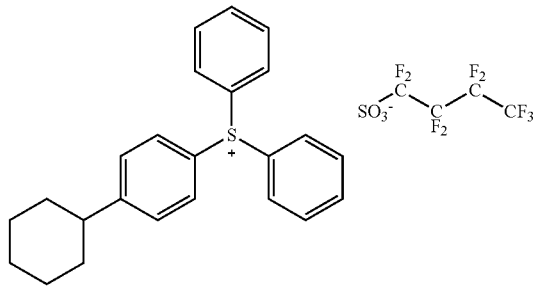

(B-2)

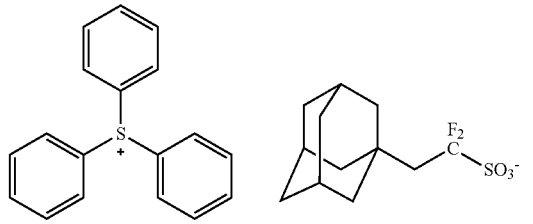

(B-5)

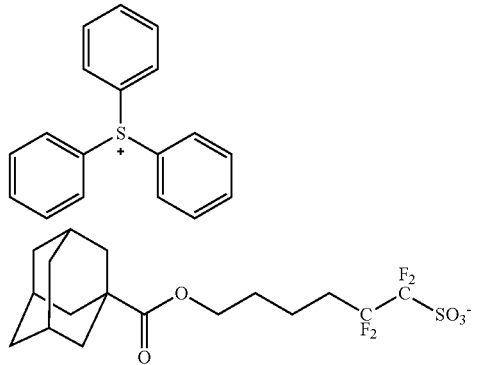

(B-6)

Acid diffusion controller (D): compounds shown by the following formulas

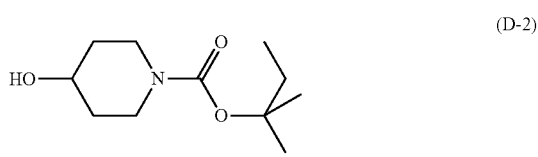

(D-2)

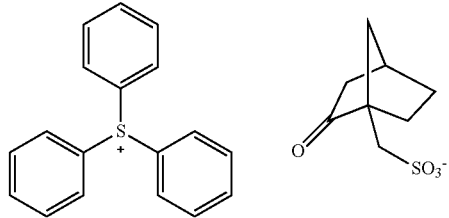

(D-4)

[Example 9]

5.0 parts by mass of the polymer (A-1), 11.0 parts by mass of the acid generator (B-2), 100.0 parts by mass of the polymer (C-1), 1.7 parts by mass of the acid diffusion controller (D-2), 100.0 parts by mass of γ-butyrolactone (additive), 1500.0 parts by mass of propylene glycol monomethyl ether acetate (solvent), and 650.0 parts by mass of cyclohexanone (solvent) were mixed to obtain a radiation-sensitive resin composition solution.

[Examples 10 to 16 and Comparative Examples 3 and 4]

A radiation-sensitive resin composition solution was obtained in the same manner as in Example 9, except for changing the composition as shown in Table 2.

10 μl/min, and the contact angle was measured every second (180 times in total). The measurement was performed after soft-baking (SB) the film at 120° C. for 50 seconds, and also performed when 10 seconds or 30 seconds had elapsed after causing the alkaline developer to come in contact with the film. The average value of twenty contact angles after the contact angle became stable was calculated, and taken as the receding contact angle (°) under the measurement conditions.

TABLE 2

| Radiation-sensitive resin composition | Polymer (A) | | Acid generator (B) | | Polymer (C) | | Acid diffusion controller | |
|---|---|---|---|---|---|---|---|---|
| | Type | Amount (parts by mass) | Type | Amount (parts by mass) | Type | Amount (parts by mass) | Type | Amount (parts by mass) |
| Example 9 | (A-1) | 5.0 | (B-2) | 11.0 | (C-1) | 100.0 | (D-2) | 1.7 |
| Example 10 | (A-1) | 5.0 | (B-5) (B-6) | 4.0 5.0 | (C-1) | 100.0 | (D-4) | 5.5 |
| Example 11 | (A-2) | 5.0 | (B-5) (B-6) | 4.0 5.0 | (C-1) | 100.0 | (D-4) | 5.5 |
| Example 12 | (A-3) | 5.0 | (B-5) (B-6) | 4.0 5.0 | (C-1) | 100.0 | (D-4) | 5.5 |
| Example 13 | (A-4) | 5.0 | (B-5) (B-6) | 4.0 5.0 | (C-1) | 100.0 | (D-4) | 5.5 |
| Example 14 | (A-5) | 5.0 | (B-5) (B-6) | 4.0 5.0 | (C-1) | 100.0 | (D-4) | 5.5 |
| Example 15 | (A-6) | 5.0 | (B-5) (B-6) | 4.0 5.0 | (C-1) | 100.0 | (D-4) | 5.5 |
| Example 16 | (A-2) | 5.0 | (B-5) (B-6) | 4.0 5.0 | (C-2) | 100.0 | (D-4) | 5.5 |
| Comparative Example 3 | (A'-1) | 5.0 | (B-5) (B-6) | 4.0 5.0 | (C-1) | 100.0 | (D-4) | 5.5 |
| Comparative Example 4 | (A'-2) | 5.0 | (B-5) (B-6) | 4.0 5.0 | (C-1) | 100.0 | (D-4) | 5.5 |

<Production and Evaluation of Resist Film>

A resist film was formed as follows using the radiation-sensitive resin composition obtained in each example or comparative example (Examples 9 to 16 and Comparative Examples 3 and 4), and the rate of reaction with an alkaline developer and development defects were evaluated using the resulting resist film. The rate of reaction was evaluated based on a change in receding contact angle with time upon contact with the alkaline developer. Development defects were evaluated by measuring the number of blob defects. The details are described below.

[Production of Resist Film]

A film was formed on a substrate using the radiation-sensitive resin composition. An 8-inch silicon wafer was used as the substrate when measuring the receding contact angle, and a 12-inch silicon wafer on which a lower-layer antireflective film ("ARC66" manufactured by Nissan Chemical Industries, Ltd.) was formed was used as the substrate when measuring the number of blob defects. The thickness of the film was 110 nm.

[Measurement of Receding Contact Angle]

The receding contact angle of the film was measured by the following method at a temperature of 23° C. (room temperature) and a humidity of 45% under atmospheric pressure using a contact angle meter "DSA-10" (manufactured by KRUS).

The needle of the contact angle meter was washed with acetone and isopropyl alcohol before the measurement. Water was injected into the needle, and the wafer was placed on the wafer stage. The height of the stage was adjusted so that the distance between the surface of the wafer and the tip of the needle was 1 mm or less. Water was discharged from the needle to form a water droplet (25 μl) on the wafer. The water droplet was sucked via the needle for 180 seconds at a rate of After performing SB under the above conditions, the film was developed for 10 seconds or 30 seconds using a 2.38 mass % tetramethylammonium hydroxide aqueous solution utilizing the GP nozzle of a developer "Clean Track ACT 8" (manufactured by Tokyo Electron Ltd.), and rinsed with purified water for 15 seconds. The substrate was then spin-dried at 2000 rpm, and the receding contact angle of the dried substrate was measured ("Receding contact angle after development for 10 seconds" and "Receding contact angle after development for 30 seconds").

[Measurement of Contact Angle after 3-Month Storage]

The resist film was stored at 23° C. for 3 months, and the receding contact angle was measured in the same manner as described above ("Receding contact angle after 3-month storage").

[Blob Defects]

The film was soft-baked (SB) at 120° C. for 50 seconds, and exposed via a line-and-space (1L/1S) mask pattern (target width: 45 nm) using an ArF immersion scanner ("NSR-S610C" manufactured by Nikon Corporation) (NA=1.3, ratio=0.800, Dipole). The exposed film was subjected to PEB at 95° C. for 50 seconds.

The film was then developed for 10 seconds using a 2.38 mass % tetramethylammonium hydroxide aqueous solution utilizing the GP nozzle of a developer "Clean Track ACT 8" (manufactured by Tokyo Electron Ltd.), and rinsed with purified water for 15 seconds. The substrate was then spin-dried at 2000 rpm to form a positive-tone resist pattern. A dose at which a 1L/1S pattern having a width of 45 nm was formed was taken as an optimum dose. A 1L/1S pattern having a width of 45 nm was formed over the entire wafer at the optimum dose to obtain a defect inspection wafer. The measurement was performed using a scanning electron microscope ("CC-4000" manufactured by Hitachi High-Technologies Corporation). The number of defects on the defect inspection wafer was measured using a system "KLA2810" (manufactured by KLA-Tencor). Defects measured using the system "KLA2351" were classified into a defect due to the resist and a defect due to foreign matter.

A case where the number of defects due to the resist film was less than 100 per wafer was evaluated as "Acceptable", a case where the number of defects due to the resist film was 100 to 500 per wafer was evaluated as "Fair", and a case where the number of defects due to the resist film was more than 500 per wafer was evaluated as "Unacceptable".

The receding contact angle measurement results and the blob defect evaluation results are shown in Table 3.

TABLE 3

| Radiation-sensitive resin composition | Receding contact angle (°) | | | Blob defects | Receding contact angle after 3-month storage (°) |
| --- | --- | --- | --- | --- | --- |
| | After SB | After development for 10 seconds | After development for 30 seconds | | |
| Example 9 | 72 | <15 | <15 | Acceptable | Did not change |
| Example 10 | 73 | <15 | <15 | Acceptable | Did not change |
| Example 11 | 73 | <15 | <15 | Acceptable | Did not change |
| Example 12 | 72 | <15 | <15 | Acceptable | Did not change |
| Example 13 | 74 | <15 | <15 | Acceptable | Did not change |
| Example 14 | 80 | <15 | <15 | Acceptable | Did not change |
| Example 15 | 78 | <15 | <15 | Acceptable | Did not change |
| Example 16 | 73 | <15 | <15 | Acceptable | Did not change |
| Comparative Example 3 | 80 | 45 | <15 | Fair | Did not change |
| Comparative Example 4 | 81 | 79 | 25 | Unacceptable | Did not change |

As shown in Table 3, the resist films formed using the radiation-sensitive resin compositions of Examples 9 to 16 including the polymer (A) according to one embodiment of the invention had a receding contact angle with water similar to those of Comparative Examples 3 and 4 after performing SB. This means that the resist films exhibit sufficient hydrophobicity during liquid immersion lithography.

In Comparative Example 3, the receding contact angle changed from 80° to 45° when the resist film was developed for 10 seconds, and decreased to less than 15° when the resist film was developed for 30 seconds. In Comparative Example 4, the receding contact angle changed slightly from 80° to 79° when the resist film was developed for 10 seconds, and decreased only to 25° even when the resist film was developed for 30 seconds. In Examples 9 to 16, the receding contact angle significantly decreased from 72 to 80° to less than 15° when the resist film was developed for 10 seconds. It was thus confirmed that the surface of the resist film formed using the composition including the polymer (A) promptly changed from a hydrophobic surface to a hydrophilic surface (surface wettability) upon contact with the alkaline developer. Specifically, it was confirmed that the surface of the resist film formed using the composition including the polymer (A) had a high rate of reaction with the alkaline developer. It is conjectured that the hydrophobic group included in the polymer (A) dissociated promptly under the alkaline conditions, so that OH groups (hydrophilic group) were unevenly distributed in the surface of the film.

The blob defect evaluation result of Comparative Example 3 was "Fair", and the blob defect evaluation result of Comparative Example 4 was "Unacceptable". On the other hand, the blob defect evaluation results of Examples 9 to 16 were "Acceptable". This suggests that a high rate of reaction with the alkaline developer was achieved in Examples 9 to 16 as compared with Comparative Examples 3 and 4, so that adhesion of impurities (e.g., development residue) to the surface of the film could be suppressed.

In Examples 9 to 16, the receding contact angle did not change even when the resist film was stored for 3 months. It was thus confirmed that the resist films of Examples 9 to 16 had excellent storage stability. Hence, the resist film formed using the composition including the polymer (A) may suitably be used to form a resist pattern.

Obviously, numerous modifications and variations of the invention are possible in light of the above teachings. It is therefore to be understood that within the scope of the appended claims, the invention may be practiced otherwise than as specifically described herein.

What is claimed is:

1. A radiation-sensitive resin composition comprising (A) a fluorine-containing compound that includes a group shown by a formula (1), and (B) a photoacid generator,

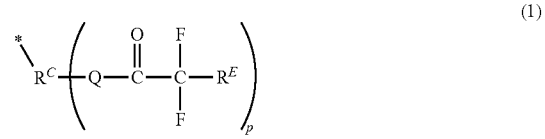

wherein $R^C$ represents a (p+1)-valent aromatic ring group, Q represents a linking group obtained by removing one hydrogen atom from a monovalent hydrophilic group, $R^E$ represents a hydrogen atom or an unsubstituted hydrocarbon group having 1 to 10 carbon atoms, p is an integer from 1 to 5, provided that a plurality of Q and a plurality of $R^E$ may respectively be either the same or different when p is an integer from 2 to 5, and "*" indicates a bonding hand.

2. The radiation-sensitive resin composition according to claim 1, wherein the fluorine-containing compound (A) is a polymer that includes a repeating unit shown by a formula (1p), (1p)

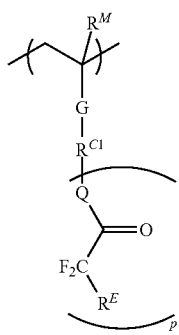

(1p-3)

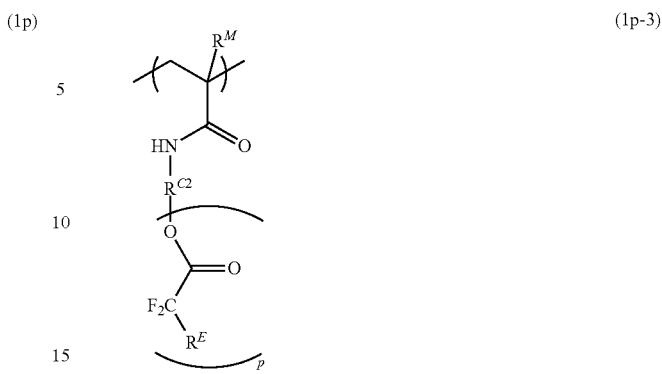

wherein $R^M$ represents a hydrogen atom, a halogen atom, an alkyl group having 1 to 5 carbon atoms, or an alkyl halide group having 1 to 5 carbon atoms, G represents a single bond, —(CH$_2$)$_b$—, —CO—O—, or —CO—NH— wherein b is 1 or 2, $R^{C1}$ represents a substituted or unsubstituted (p+1)-valent aromatic ring group, Q represents a linking group obtained by removing one hydrogen atom from a monovalent hydrophilic group, $R^E$ represents a hydrogen atom or an unsubstituted hydrocarbon group having 1 to 10 carbon atoms, and p is an integer from 1 to 5, provided that a plurality of Q and a plurality of $R^E$ may respectively be either the same or different when p is an integer from 2 to 5.

3. The radiation-sensitive resin composition according to claim 2, wherein the fluorine-containing compound (A) is a polymer that includes a repeating unit shown by a formula that is selected from the group consisting of formulas (1p-1) to (1p-3), (1p-1)

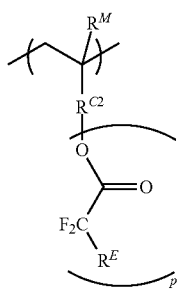

(1p-2)

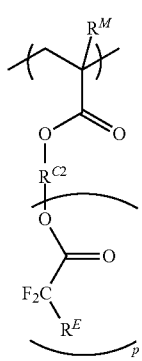

wherein $R^M$ represents a hydrogen atom, a halogen atom, an alkyl group having 1 to 5 carbon atoms, or an alkyl halide group having 1 to 5 carbon atoms, $R^{C2}$ represents a substituted or unsubstituted (p+1)-valent benzene ring, $R^E$ represents a hydrogen atom or an unsubstituted hydrocarbon group having 1 to 10 carbon atoms, and p is an integer from 1 to 5, provided that a plurality of $R^E$ may be either the same or different when p is an integer from 2 to 5.

4. The radiation-sensitive resin composition according to claim 3, wherein the fluorine-containing compound (A) is a polymer that includes a repeating unit shown by a formula that is selected from the group consisting of formulas (1p-1-1) to (1p-3-1),

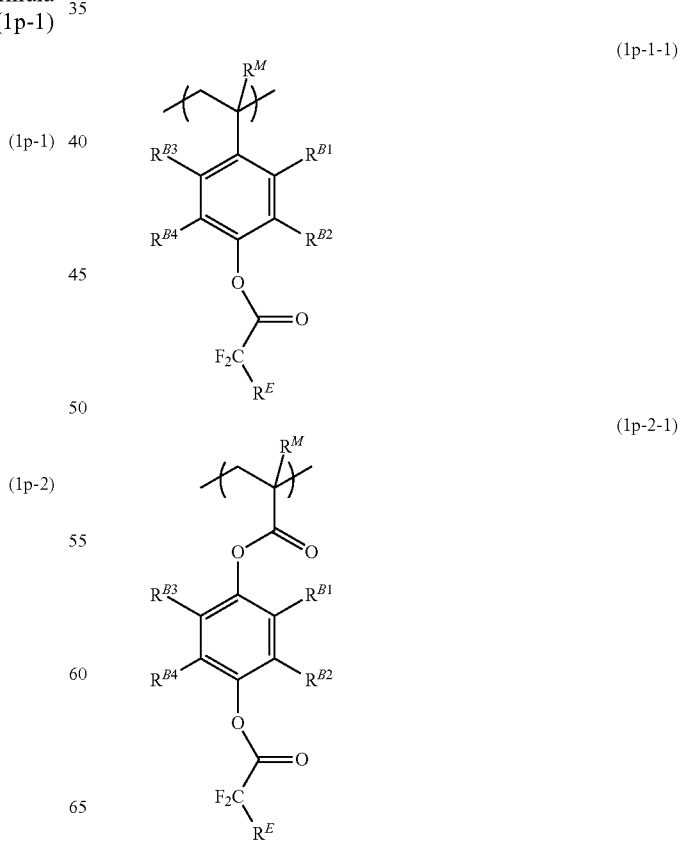

-continued (1p-3-1)

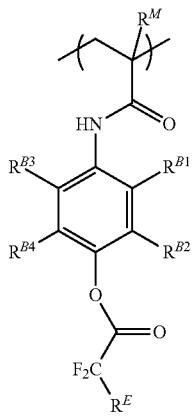

wherein $R^{B1}$ to $R^{B4}$ individually represent a hydrogen atom, a fluorine atom, $-R^{P1}$, $-R^{P2}-O-R^{P1}$, $-R^{P2}-CO-R^{P1}$, $-R^{P2}-CO-OR^{P1}$, $-R^{P2}-O-CO-R^{P1}$, $-R^{P2}-OH$, $-R^{P2}-CN$, or $-R^{P2}-COOH$ wherein $R^{P1}$ represents a monovalent chain-like saturated hydrocarbon group having 1 to 10 carbon atoms, a monovalent alicyclic saturated hydrocarbon group having 3 to 20 carbon atoms, or a monovalent aromatic hydrocarbon group having 6 to 30 carbon atoms, provided that some or all of the hydrogen atoms of these groups may be substituted with a fluorine atom, and $R^{P2}$ represents a single bond, a divalent chain-like saturated hydrocarbon group having 1 to 10 carbon atoms, a divalent alicyclic saturated hydrocarbon group having 3 to 20 carbon atoms, a divalent aromatic hydrocarbon group having 6 to 30 carbon atoms, or a group obtained by substituting some or all of the hydrogen atoms of these groups with a fluorine atom, and $R^E$ represents a hydrogen atom or an unsubstituted a-hydrocarbon group having 1 to 10 carbon atoms.

5. The radiation-sensitive resin composition according to claim 1, further comprising (C) a polymer that includes an acid-labile group, wherein the fluorine-containing polymer (A) has a fluorine atom content higher than that of the polymer (C).

6. A method for forming a resist pattern comprising forming a resist film on a support using the radiation-sensitive resin composition according to claim 1, subjecting the resist film to liquid immersion lithography, and developing the resist film subjected to liquid immersion lithography to form a resist pattern.

7. A polymer comprising a repeating unit shown by a formula (1p),

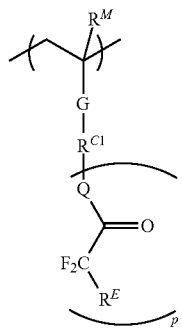

(1p)

wherein $R^M$ represents a hydrogen atom, a halogen atom, an alkyl group having 1 to 5 carbon atoms, or an alkyl halide group having 1 to 5 carbon atoms, G represents a single bond, $-(CH_2)_b-$, $-CO-O-$, or $-CO-NH-$ wherein b is 1 or 2, $R^{C1}$ represents a (p+1)-valent aromatic ring group, Q represents a linking group obtained by removing one hydrogen atom from a monovalent hydrophilic group, $R^E$ represents a hydrogen atom or an unsubstituted hydrocarbon group having 1 to 10 carbon atoms, and p is an integer from 1 to 5, provided that a plurality of Q and a plurality of $R^E$ may respectively be either the same or different when p is an integer from 2 to 5.

8. A compound shown by a formula (1m),

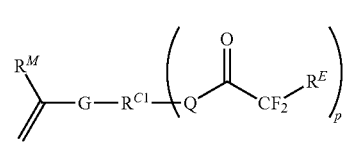

(1m)

wherein $R^M$ represents a hydrogen atom, a halogen atom, an alkyl group having 1 to 5 carbon atoms, or an alkyl halide group having 1 to 5 carbon atoms, G represents a single bond, $-(CH_2)_b-$, $-CO-O-$, or $-CO-NH-$ wherein b is 1 or 2, $R^{C1}$ represents a (p+1)-valent aromatic ring group, Q represents a linking group obtained by removing one hydrogen atom from a monovalent hydrophilic group, $R^E$ represents a hydrogen atom or an unsubstituted a-hydrocarbon group having 1 to 10 carbon atoms, and p is an integer from 1 to 5, provided that a plurality of Q and a plurality of $R^E$ may respectively be either the same or different when p is an integer from 2 to 5.

9. The radiation-sensitive resin composition according to claim 1, wherein $R^C$ represents a substituted (p+1)-valent aromatic ring group.

10. The polymer according to claim 7, wherein $R^{C1}$ represents a substituted (p+1)-valent aromatic ring group.

11. The compound according to claim 8, wherein $R^{C1}$ represents a substituted (p+1)-valent aromatic ring group.

* * * * *